United States Patent [19]

Auth

[11] E Patent Number: Re. 32,821

[45] Reissued Date of Patent: Jan. 3, 1989

[54] APPARATUS AND METHOD FOR PHOTOLUMINESCENCE ANALYSIS

[76] Inventor: Gerald L. Auth, 2858 Chillon Way, Laguna Beach, Calif. 92651

[21] Appl. No.: 9,253

[22] Filed: Jan. 12, 1987

Related U.S. Patent Documents

Reissue of:

[64] Patent No.: 4,562,356
Issued: Dec. 31, 1985
Appl. No.: 641,835
Filed: Aug. 17, 1984

U.S. Applications:

[63] Continuation-in-part of Ser. No. 555,607, Nov. 28, 1983, abandoned.

[51] Int. Cl.[4] ..... G01J 3/00

[52] U.S. Cl. ..... 250/458.1; 250/341; 250/459.1

[58] Field of Search ..... 356/346; 250/459.1, 250/458.1, 358.1, 341, 339, 347, 351, 352

[56] References Cited

U.S. PATENT DOCUMENTS

| | | | |
|---|---|---|---|
| 4,108,716 | 8/1978 | Pritchard et al. | 156/636 |
| 4,492,871 | 1/1985 | Tajima | 250/459.1 |
| 4,542,295 | 9/1985 | Mattson et al. | 250/352 |

FOREIGN PATENT DOCUMENTS

| | | | |
|---|---|---|---|
| 0117012 | 7/1982 | Japan | 250/352 |

OTHER PUBLICATIONS

S. M. Davidson, T. J. Cumberbatch, E. Huang, and S. Myhajlenko, "A New Scanning Cathodoluminescence Microprobe System", *Institute of Physics Conf. Ser. No. 60, Sect. 4*; Paper presented at Microsc. Semicond. Mater. Conf., Oxford, England [GB] (10 Apr. 1981) pp. 191–196.

T. J. Cumberbatch, S. M. Davidson, and S. Myhajlenko, "Cathodoluminescence Imaging of Silicon", *Institute of Physics Conf. Ser. No. 60, Sect. 4*; Paper presented at Microsc. Semicond. Mater. Conf., Oxford, England [GB] (10 Apr. 1981) pp. 197–202.

W. K. Yuen and G. Horlick, "Atomic Spectrochemical Measurements with a Fourier Transform Spectrometer", *Analytical Chemistry*, vol. 49, No. 9 (Aug. 1977) pp. 1446–1448.

R. H. Hancock and D. J. Baker, "Infrared Prism Interferometer Spectrometer Using a Gas-Lubricated Drive Bearing", *Infrared Physics, vol. 14, No. 4 (Nov. 1974) pp. 259–269.*

J. F. Black, C. J. Summers, and B. Sherman, "Scanned-Laser Microscope for Photoluminescence Studies", *Applied Optics, vol. 11, No. 7 (Jul. 1972) pp. 1553–1562.*

(List continued on next page.)

*Primary Examiner*—Janice A. Howell
*Assistant Examiner*—Constantine Hannaher
*Attorney, Agent, or Firm*—Thomas L. Plante

[57] ABSTRACT

An apparatus, for photo-luminescent analysis of the surface of crystalline silicon, is disclosed, in which the photons emitted from the sample are passed through a two-beam (or two-arm) interferometer, having the usual beamsplitter, fixed mirror, and movable mirror. The interferometer output is directed to a detector which is a germanium photo-diode, cooled in a Dewar, which also cools the initial electronic circuitry to which the detector output is input. Using the disclosed apparatus, methods are available for readily eliminating the negative effect of the electron-hole-dropler phenomenon, and for utilizing the [no-photon] *no-phonon* region of the spectrum to identify otherwise unidentified impurity (or dopant) materials.

* * * * *

The questions raised in reexamination request No. 90/001,324, filed Sep. 9, 1987, have been considered and the results thereof are reflected in this reissue patent which constitutes the reexamination certificate required by 35 U.S.C. 307 as provided in 37 CFR 1.570(e).

46 Claims, 21 Drawing Sheets

OTHER PUBLICATIONS

Mme Janine Connes, "Spectroscopic Studies Using Fourier Transformation", U.S. Naval Ordnance Test Station, NAVWEPS Repact 8099, China Lake, California (Jan. 1963) pp. 139-148, [Translation from the French of *Revue d'Optique,* vol. 40 (1961)].

James L. Lauer, Melvin E. Peterkin, "Infrared Emission Micro-Interferometry-Evidence for Alignment of Fluid Bearing Lubricants", *American Laboratory,* vol. 9, No. 11 (Nov. 1977), pp. 29-37.

Hammond, R. B. et al., "Onsets of the Electron-Hole Droplet Luminescence in ", *Physical Review Letters,* vol. 42, No. 8, (Feb. 1979), pp. 523-526.

Mertz, L., "Improved Polarization Interferometer for Fourier Spectroscopy", *Optics Communications, vol. 6, No. 4 (Dec. 1972), pp. 353-355.*

*Transformations in Optics,* John Wiley and Sons (1965), New York, pp. 1-16.

Sakai, H., "Consideration of the Signal to Noise Ratio in Fourier Spectroscopy", Aspen Int'l. Conference on Fourier Spectroscopy (1970), pp. 19, 28.

Thewalt, M. L. W., "Details of the Structure of Bound Excitons and Bound Multiexciton Complexes in Si", *Canadian Journal of Physics,* vol. 55, No. 17 (Sep. 1977), pp. 1463-1480.

Vanasse, G. A. et al, *Spectrometric Techniques,* Academic Press (1977), vol. 1, pp. 1-3, 24-28, 69-70 et al.

Wolfe, J. P. et al., "Excitonic Matter", *Scientific American (Mar. 1984), pp. 98-107.*

FIG. 7
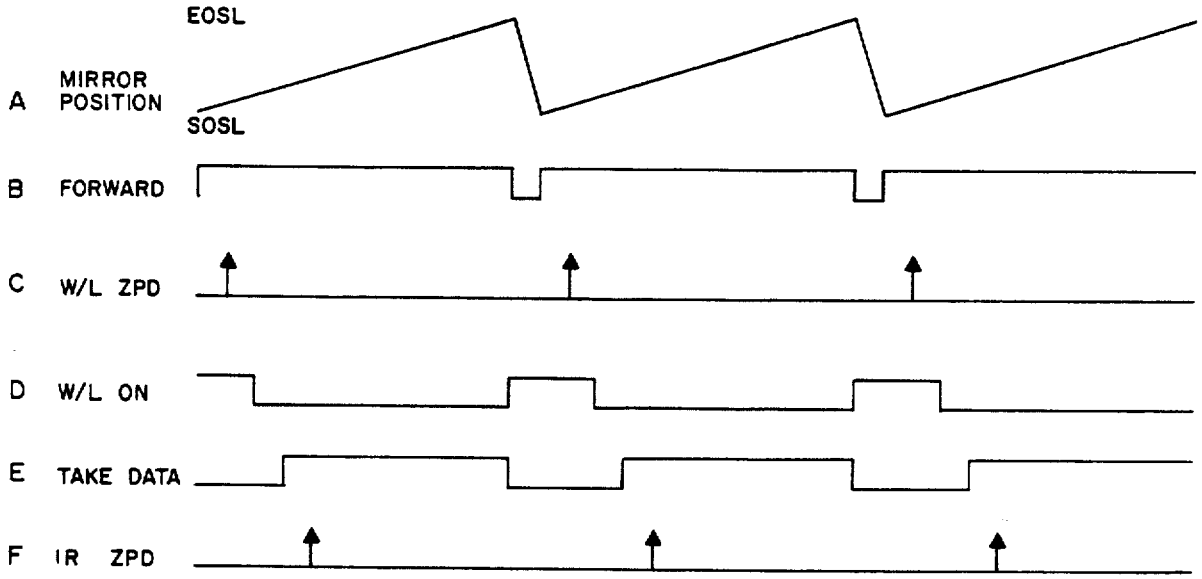
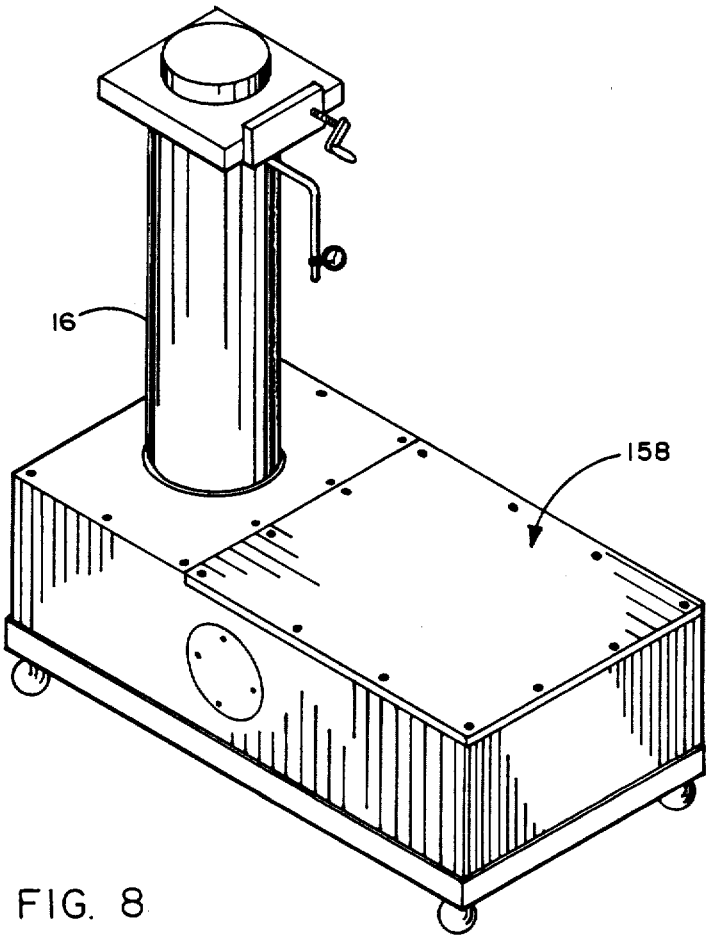
FIG. 8

$P_{NP}$ (BE)
NO As
8600
8700
8800
8900
9000
9100
9200
9300

$P_{NP}$(BE)
$As_{NP}$(BE)
$I_{TO}$ (FE)
$B_{TO}$(BE)
$P_{TO}$(BE)
$I_{LO}$(FE)
$B_{TO}(b_1)$
$B_{TO}(b_2)$
$B_{TO}(b_3)$
8600
8700
8800
8900
9000
9100
9200
9300

APPARATUS AND METHOD FOR PHOTOLUMINESCENCE ANALYSIS

Matter enclosed in heavy brackets [ ] appears in the original patent but forms no part of this reissue specification; matter printed in italics indicates the additions made by reissue.

This application is a continuation-in-part of Auth U.S. application Ser. No. 555,607, filed Nov. 28, 1983, abandoned.

BACKGROUND OF THE INVENTION

This invention relates to the field of photoluminescence (PL) analysis, in which a light source is used to excite a sample, and the photons emitted by the sample are passed through a spectrometer which provides desired spectral information.

Although its potential uses ae much broader, the primary concern of the present invention relates to the determination of impurity concentrations in single crystal silicon (Si), whether such impurities are intentionally or unintentionally present in the silicon. These impurity determinations are an important means of evaluating the characteristics of electronic devices in integrated circuit chips. The use of PL analysis is essentially directed at determining surface characteristics, whereas other types of analysis [ae] *are* used in determining bulk silicon characteristics.

In U.S. patent application Ser. No. 411,603, also filed by the present applicant (on Aug. 26, 1982), [abandoned,] the use of the PL technique for surface analysis of silicon crystal impurities is discussed at length. Both the value of this technique, and the problem of getting sufficient radiation throughput to the detector, are pointed out in that application.

Even with the improvements disclosed in Application Ser. No. 411,603, the PL analysis of silicon chip impurities is subject to significant deficiencies. The present application is intended to deal with those deficiencies by providing a fundamentally different approach to the problem of PL analysis of silicon (and potentially other materials).

The wavelength range of the radiation which needs to be measured is in a very "awkward" part of the spectrum. It covers approximately the range of 1.07 through 1.127 microns, which makes the system subject to all the measurement problems of both the visible and infrared portions of the spectrum.

A major problem is the wavelength limitation of the available photomultiplier (PM) detector tubes. These tubes, such as the S1 photo-cathode tube, have a very desirable signal-to-noise ratio because of their large, essentially noise-free, amplification. But [there] *their* sensitivity begins to fall off rapidly in the portion of the spectrum which is particularly relevant for PL analysis of silicon surface impurities. FIG. 1 of the drawings is a graph which shows the response characteristics of the available PM tubes as a dashed line curve A. The wavelengths are plotted on the X-axis and the responsiveness of the tubes is plotted on the Y-axis. As is apparent from FIG. 1, the signal from the S1 tube, which is the best available PM tube, begins to drop off rapidly at a wavelength of about 0.9 microns.

In order to provide a detector having a wavelength range which comfortably includes the significant portion of the spectrum in silicon PL analysis, the PM tube and its amplification (or gain) advantage apparently need to be eliminated. Substituting a photo-voltaic detector having the desired wavelength characteristics, such as germanium, eliminates the signal-to-noise benefits derived from the PM tube's high noise-free internal amplification.

Reduction of the usable signal in a system of the type disclosed in Aplication Ser. No. 411,603 would seriously aggravate the radiation throughput deficiency inherent in PL silicon analysis systems having grating monochromators. So a means of substantially increasing the radiation throughput between the sample and the detector is necessary for advancement of the art of PL analysis. This application, and its parent application, Ser. No. 555,607, provide solutions for the problems indentified above.

Furthermore, the continuing use of the system disclosed in Application Ser. No. 555,607 has resulted in such a large and unexpected improvement in PL analysis that heretofore unsuspected limitations, or deficiencies, in monochromator systems have become apparent. Three major deficiencies, previously unsuspected, have now become apparent.

One such deficiency in monochromator PL systems is due to the extremely rapid diffusion of the excitons in the semiconductor crystal. The excitons are transient entities in the crystal, which are caused by the laser excitation photons, and which, in turn, cause emission of photons by the crystal. Because of the exciton diffusion, and consequent wider spatial distribution diffusion of the crystal-emitted photons, a monochromator used for PL analysis is, in fact, doomed to inadequacy because it cannot capture enough of the crystal-emitted light. The characteristics of excitons in semiconductor crystals are discussed in an article titled "Excitonic Matter" by Wolfe and Mysyrowicz in the March, 1984 issue of Scientific American (pages 98–107). This article states that "each laser pulse creates a new cloud of excitons that diffuses and decays before the next pulse is generated". The article further explains that "the excitons diffuse like a dilute gas of atoms. The diffusion constant for an exciton gas, however, is much larger than it is for an ordinary atomic gas. (text omitted) The extremely fast diffusion of the exciton is a result of its small mass and its relatively infrequent scattering by other particles at low temperatures."

A second deficiency in monochromator PL systems, which was not perceived until the present invention was developed, is the absence of acceptable calibration, i.e., comparability of results from sample to sample. As a result of a spectacular improvement in sensitivity, i.e., signal-to-noise ratio, attained by using the apparatus of the present invention, as well as the extended spectral coverage, it is now apparent that the "electron hole droplet" (EHD) phenomenon has heretofore effectively destroyed sample-to-sample calibration. The EHD phenomenon is discussed in the previously cited article and also in an article titled "Onsets of the EHD Luminescence in Si" by Hammond and Silver in Physical Review Letters (American Physical Society), Volume 42, Number 8 (Feb. 19, 1979, pages 523–526). The latter article predicts, by extrapolation, the point of onset of EHD luminescence as laser intensity on the semiconductor surface is increased. The significance of the EHD effect relates to the excitonic gas density induced in the sample. This gas density has been seen to vary dramatically from sample to sample for a given laser excitation level, affecting the relative intensities of the free exciton to the bound exciton lines. Since the quantitative measurement of impurity concentration is calculated from these relative intensities, the changing excitonic gas density effectively destroys the calibration of the measurement.

A third deficiency in monochromator PL systems, which the present invention spotlights, is the limitation of results forced by the need to largely sacrifice certain parameters as a trade-off for those considered vital. Specifically, in spectrometry, there are four parameters which represent desirable goals—(1) sensitivity, (2) speed of data acquisition, (3) resolution, and (4) spectral coverage. In monochromator PL systems, it is necessary to maximize sensitivity and speed of data acquisition. It has, therefore, been necessary for such systems to accept whatever is available in the other two parameters—resolution and spectral coverage. This has severely limited the information produced by monochromator PL systems, to an extent not even suspected until the advent of the present invention.

SUMMARY OF THE INVENTION

The present invention controverts the assumptions heretofore followed by combining a photo-luminescent input from the sample with an interferometer (replacing the grating monochromator) and a detector having a wavelength sensitivity band which is fully adequate to supply the desired spectral information. In other words, nondispersive spectroscopy is substituted for dispersive spectroscopy. For reasons which will be discussed below, it has heretofore been assumed that PL systems for silicon surface analysis do not constitute appropriate uses for interferometers (i.e., for non-dispersive spectroscopy).

The present invention also deals with solutions of the two major problems inherent in the new PL system described in the preceding paragraph: (1) preventing extraneous radiation (i.e., radiation other than the sample-emitted photons) from reaching the detector; and (2) obtaining a satisfactory signal-to-noise ratio in the detector output, without having the benefits of a photomultiplier tube.

The present invention has proved to have a better signal-to-noise ratio (sensitivity) than the monochromator PL systems by at least three orders of magnitude for a given choice of data collection parameters. This very surprising benefit, the reasons for, and results of, which will be discussed below, permits the present PL system to essentially avoid trade-offs among parameters, and to provide radically better results in all four parameters: sensitivity, speed of data acquisition, resolution, and spectral coverage.

Furthermore, the very extensive improvements provided by the present invention clearly display in the spectra the effects of the electron hole droplet (EHD) problem; and they have also provided a means for substantially eliminating the problem by reducing the power of the laser excitation beam until the EHD problem substantially disappears.

In sum, the present invention, which is referred to as the Fourier Transform Photoluminescence (FTPL) system, has the following advantages over prior PL systems:

(a) Higher sensitivity—FTPL allows use of reduced excitation power without sacrificing "spectral quality" or data collection time.

(b) Resolution—higher resolution can be obtained by FTPL without sacrificing optical throughput as in the case of monochromator systems.

(c) Spectral coverage—FTPL allows much greater spectral coverage than monochromator systems, with no sacrifice of data collection time.

(d) Speed—speed of data acquisition allows many spectra of one sample to be taken at differing excitation intensities, enabling the operator to select the optimal power level for a given sample. This speed also allows much more high-information-content spectra to be obtained, enabling the state-of-the-art in PL analysis to advance much more rapidly. This includes not only the development of better hardware and software, but enhances understanding of the underlying excitonic dynamics involved in the phenomenon.

It would be difficult to overstate either the value of FTPL-related discoveries, or the potential of FTPL for maturation and enhancement of the PL technique of semiconductor analysis.

BRIEF DESCRIPTION OF THE DRAWINGS

FIG. 7 is a timing diagram showing the sequence of events during successive spectral scans; and FIG. 8 is an outline drawing of the system hardware showing the cover which encloses the entire system;

DETAILED DESCRIPTION OF PREFERRED EMBODIMENT

Figure 2:
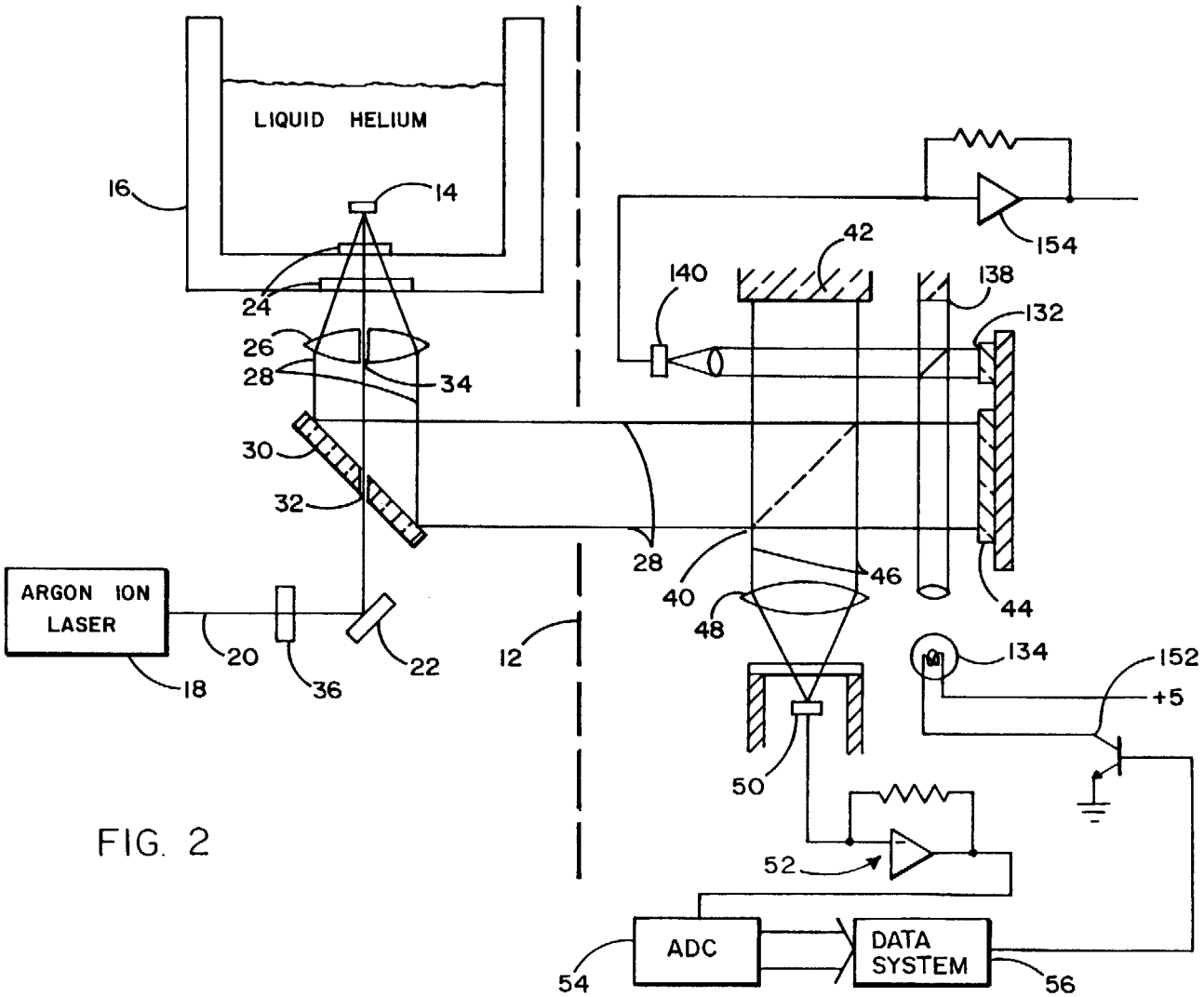
FIG. 2 is a diagrammatic showing of a silicon surface analyzing apparatus (FTPL) combining an input portion which cause photo-luminescent sample excitation with an analytical portion having a two-beam (or two-arm) interferometer.

In FIG. 2, which shows the FTPL invention in diagrammatic form, a vertical dashed line 12 is used to separate the photo-luminescent input portion from the interferometer which provides spectrally scanned throughput to the detection and electronic output portion.

As described in Application Ser. No. 411,603, a sample 14 (silicon crystal) is immersed in liquid helium inside a Dewar container 16, where its temperature is maintained at the required low temperature for successful photoluminescent (PL) excitation of the sample. Reference is made to the prior application for a detailed explanation of the PL process. The PL process relies on analysis of the sample-emitted photons for information, rather than analysis of source radiation after it has illuminated the sample. The PL process is particularly useful to provide information not readily obtainable in a "bulk" analysis process, in which "absorption" of source-emitted radiation by the sample is measured at the detector (rather than sample-emitted "excitation" radiation).

The radiation source used to provide excitation of the silicon sample is preferably an argon ion laser 18, whose monochromatic radiation beam 20 is reflected by a mirror 22 toward sample 14. The laser beam 20 enters the Dewar container 16 through suitable windows 24, as described in the prior application.

The energy of the laser beam 20 causes photoexcitation of the surface of sample 14, which emits photons, in accordance with the process described in the prior application. A substantial portion of the scattered photons are collected and collimated by a lens (or multilens optics) 26; and the collimated beam 28 leaving the collecting/collimating lens 26 is then reflected by a mirror 30 toward the interferometer portion of the apparatus. The mirror 30 has an aperture 32 which permits laser beam 20 to reach the sample, and which also lets specular reflection of the laser beam (from the sample surface) pass out of the system instead of entering the spectrometer.

An aperture 34 is provided in the center of collecting-/collimating lens 26. This aperture is important to prevent lens 26 from acting as a focusing lens for the laser beam 20. If the laser beam passed through lens 26, the energy concentration of the beam at the sample would tend to have a decalibrating effect on the analysis.

Radiation from laser generator 18 is isolated from the interferometer by enclosure of the laser in a cavity and by passing the laser beam 20 through a filter 36, which removes plasma lines, leaving only the desired green line of radiation in the apparatus (for sample surface photoexcitation).

The sample-emitted photons collected and collimated by lens (or lens system) 26 are reflected by mirror 30 to provide a collimated radiation beam 28 entering the interferometer. The interferometer has the usual beamsplitter 40, which partially reflects and partially transmits the entering radiation, causing radiation to enter the two arms of the interferometer. A fixed mirror 42 returns the radiation in one interferometer arm, and a movable mirror 44 returns the radiation in the other interferometer arm.

Returning radiation in the two interferometer arms is recombined at the beamsplitter 40, and a substantial portion of the recombined radiation provides a collimated beam 46 which is focused by a lens (or lens system) 48 on a detector 50. The electronic signals from the detector are input to a pre-amp 52, whose output is input to an electronics processing system, including an analog-to-digital converter 54 and a data processing system 56.

Because of the characteristics of the input radiation, an interferometer used in the manner disclosed in this application requires: (a) very accurate mechanical/optical functioning to accommodate the short wavelengths of the radiation; and (b) very complete blocking of any entraneous radiation to avoid falsification of the input at detector 50.

Figure 3:
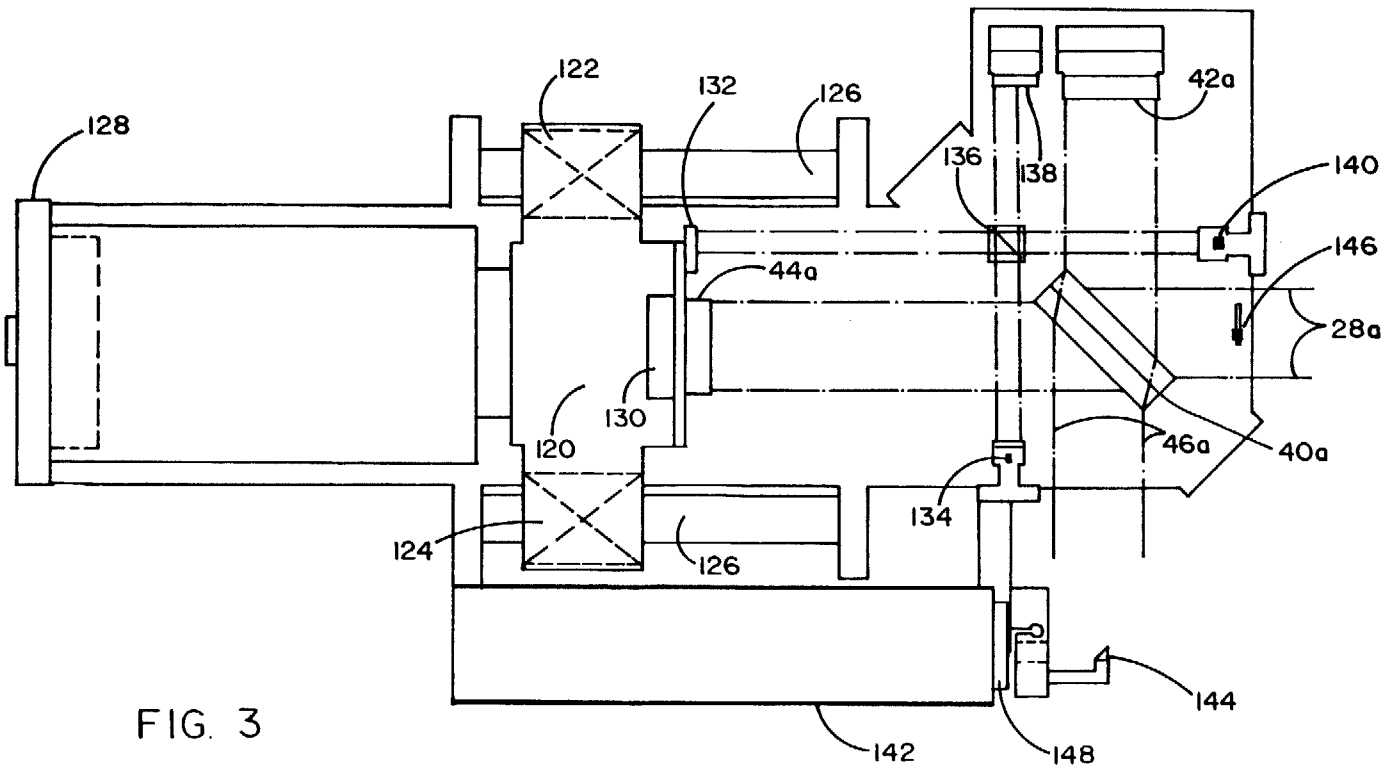
FIG. 3 is a more detailed showing of a high performance interferometer suitable for use in a PL analysis system.

The high-performance interferometer marketed by the assignee of this application, Midac Corporation, has proved to be suitable for use in the disclosed system. A diagrammatic illustration of a Midac interferometer is shown in FIG. 3. It will be described in detail below.

There are four sources of extraneous, or undesired, radiation, all of which need to be blocked from access to detector 50. They include ambient radiation, radiation from the sample-excitation laser 18, and two of the three radiation beams in the interferometer itself. The interferometer generally includes three radiation sub-systems: (1) the radiation which constitutes the basic analytical beam; (2) a monochromatic (laser) beam which produces a periodic fringe pattern from which pulses are derived to "clock" the sampling of detector signals by the computer system; and (3) a wideband, or "white" light beam which is used to start the sampling in each scanning sweep of the basic analytical beam at the identical (and appropriate) point in the stroke.

The latter two require special handling in the present system. The laser clock-providing beam can be filtered, and the laser generator which emits it can be enclosed. The white light beam, which is only required to start the analytical scan, can be turned off during the analytical scan, and then turned on during the return of the movable mirror 44 between successive scans.

Interferometers have generally been confined to use in the far-to-mid infrared radiation region, and have not been considered desirable in or near the visible radiation region. A major reason for this is the problem of mechanical tolerances when shorter wavelengths are involved. In the present apparatus the alignment accuracy of the interferometer should, if possible, be maintained at 0.1 of the signal wavelength. This is a much tighter tolerance specification than is needed in the normal infrared region of interferometer use.

Also, one of the advantages of interferometers has not heretofore been significant in the shorter wavelength region. Interferometers' primary advantages over grating monochromators are: (a) their "throughput" advantage (also called "Jacquinot's" advantage), and (b) their "multiplex" advantage (also called "Fellgett's" advantage). The multiplex advantage, i.e., the fact that all wavelengths are continually "seen" at the detector, is useful in improving the signal-to-noise ratio of the output. However, in shorter wavelength systems, photomultiplier tubes have heretofore been generally used. Their inherently high signal-to-noise ratio output causes the multiplex advantage of an interferometer to be substantially meaningless (although it does not reduce the value of the throughput advantage).

Interferometers have been used in analysis of silicon materials, but only in infrared bulk analysis apparatus (as distinguished from surface analysis), and only in apparatus in which the detected radiation is sample-illuminating radiation emanating from a source other than the sample. The present invention appears to be the first effort to combine PL surface analysis of silicon with an interferometer.

The initial analysis of the sensitivity (i.e., signal-to-noise ratio) to be expected from the Fourier Transform PL system (FTPL) of the present invention, as compared to a monochromator PL system, predicted about a two to one improvement. Instead, radically increased sensitivity has been experienced, amounting to an effective improvement of three orders of magnitude (1000 to 1). The performance of the FTPL disclosed in this application offers: (1) at least 1000 times greater signal-to-noise performance than monochromator-based systems operated at the same resolution and data acquisition time, (2) extended spectral coverage ($\sim$0.75 $\mu$m to $\sim$1.6 $\mu$m with a Ge photodiode detector), and (3) higher resolution (0.05 $cm^{-1}$ max.), capabilities which make the present FTPL the only true high-performance photoluminescence system.

The increased sensitivity allows use of lower sample excitation intensities, important in preventing the formation of the electron-hole liquid or droplet (EHD), which "robs" the shallow-impurity emission intensities, and therefore must be controlled for quantitative analysis. Extended spectral coverage allows other deep-level phenomena to be observed, many of which are topics of great research interest at this time. Also, the ease of data presentation and magnification of spectral features allows unequivocal determination of shallow-impurity species, especially important for the sharp, closely spaced features in the "no phonon" region of the spectrum.

It is believed that the compensation of the interferometer field-of-view for the exciton diffusion problem is a major cause of the sensitivity improvement over monochromator PL systems. Another possible cause is the reduction in the number of optical elements, particularly coated elements, which enhances sensitivity. Furthermore, it appears that the PM tubes used in monochromator-based systems have not been performing as well as assumed.

As discussed in the Background of the Invention, it has been learned that the extremely rapid diffusion of the excitons produced by the laser photons in the silicon crystal, causes the crystal-emitted photons to be so spread out that a monochromator cannot obtain adequate throughput to the detector. The interferometer has a sufficiently large acceptance area, i.e., detector image on the sample, to compensate for the exciton diffusion.

Diffusion of excitons has been observed to be considerable in uniaxially stressed silicon. Recent experiments with the prior monochromator-based PL system have indicated that the extent of excitonic diffusion in unstressed silicon is greater than expected. In the monochromator system, the focusability of the luminescence was important in obtaining the best optical throughput, i.e., the most luminescent light through the system to the detector. Since the excitons diffuse, much of the signal is lost at the input slit of the monochromator. The large acceptance area of the interferometer allows this diffused excitonic radiation to reach the detector very efficiently. This is the major reason for the dramatic improvement in sensitivity obtained with the FTPL.

The combination of an interferometer with a PL source of radiation allows a detector to be used which has an appropriate wavelength range to measure effectively the radiation which is of particular interest in surface analysis of silicon. In order for the desired measurements to remain comfortably within the range of the detector, it should have a range which extends to wavelengths of about 1.5 microns, which is not generally attainable with photomultiplier tubes.

Several types of photo-detectors provide an adequate range of wavelengths. It appears that a particularly useful detector for the purposes of the present apparatus is a germanium photo-diode. A typical performance curve of such a photo-voltaic diode is shown by the solid line in FIG. 1, which shows a substantially flat performance curve between 0.8 micron wavelength and 1.45 micron wavelength (below 0.8 the performance curve would not fall off rapidly). The wavelengths of primary interest in PL analysis of silicon surfaces are well within the range of the germanium photo-diode. (Other types of photo-diodes which might be considered are indium antimonide, lead selenide, mercury cadmium telluride, and indium arsenide).

As compared with a PM tube, the germanium photo-diode has relatively poor performance from a signal-to-noise standpoint. However, the multiplex advantage of the interferometer helps to overcome this disadvantage. Additionally, by locating the first stage of the preamplifier 52, which receives the output signal from detector 50, in the same cooled container as the detector, the noise problem is reduced.

The interferometer inherently provides a tremendous throughput advantage over a grating monochromator, i.e., an improvement on the order of 50 to 1. As previously explained, the exciton diffusion effect multiplies the significance of this throughput advantage. This greatly enhances the quality of the information provided by the apparatus, in addition to the benefit of comfortably including the desired wavelength range in the spectral information output.

Although a photomultiplier tube has a high amplification factor, which is not present in the photo-diode, the photo-diode compensates by having a very impressive quantum efficiency advantage (approximately a 10,000 to 1 ratio) over the tube in the wavelength range of interest. Whereas, only one photoelectron is generated by the photo-cathode of the tube for approximately 10,000 incoming photons, the quantum efficiency of the photo-diode approaches unity, i.e., the ratio of hole-electron pairs generated by the diode is approximately 0.8 of the number of incoming photons.

Figure 5:
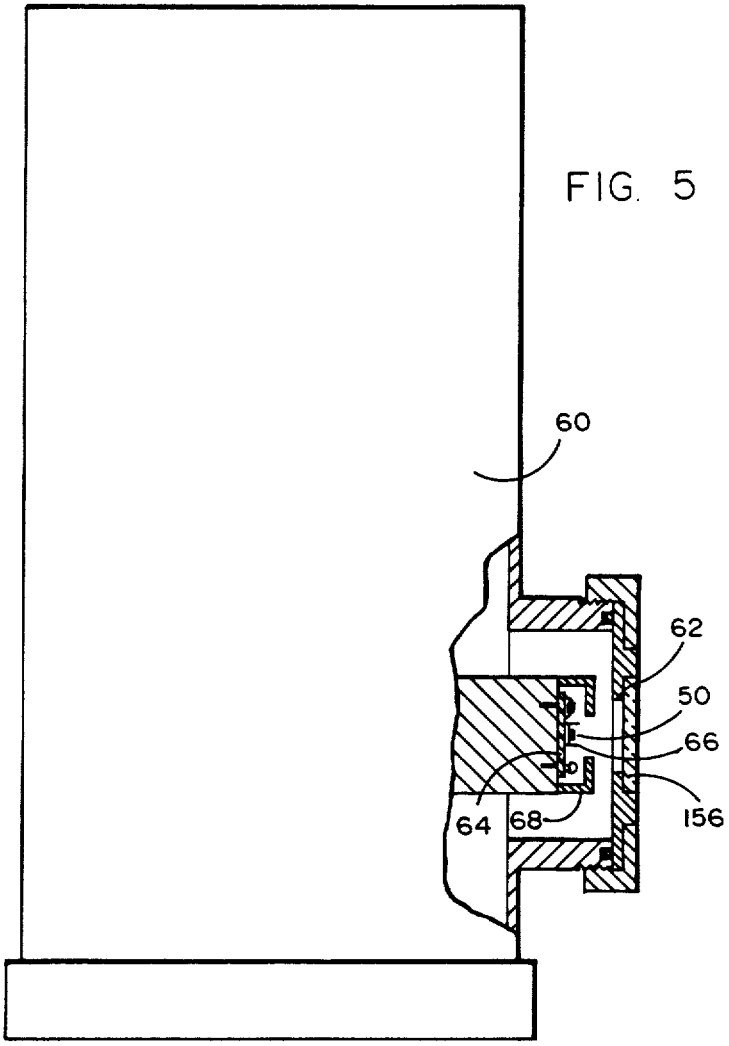
FIG. 5 shows the detector and pre-amp of the signal output portion of the FTPL system mounted in a cooling structure for noise control purposes.

An advantage of the germanium photo-diode is its compactness. As shown in FIG. 5, detector 50 is mounted inside a "side-looker" Dewar container 60, having a window 62 which admits incoming radiation to the detector. The Dewar 60 is preferably liquid nitrogen cooled, i.e., having a temperature of approximately 77° K.; a temperature range of 50° K. to 150° K. appears to be acceptable. The detector is shown supported on a circuit board 64, which also carries the cooled portion of the pre-amplifier circuitry. For its protection, the detector is inside a TO-3 transistor can 66. In order to shield the detector 50 and the first stage of the pre-amplifier circuitry from heat radiation, a metal radiation shield 68 may be used.

Figure 6A:
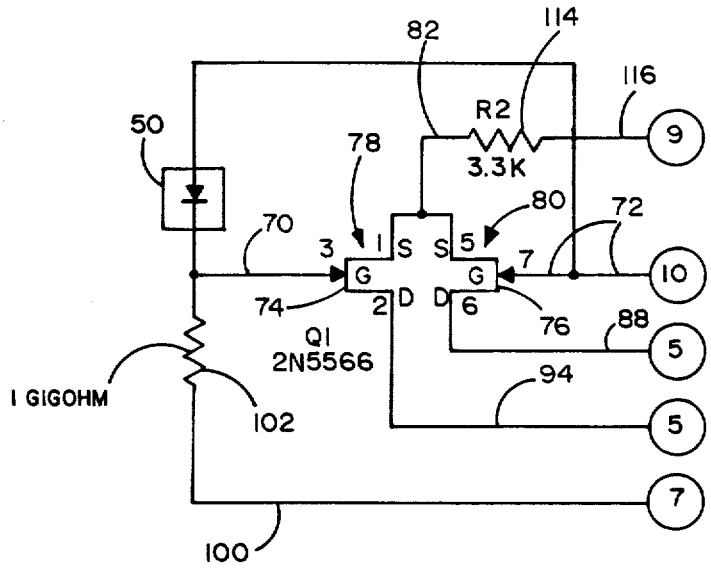
FIG. 6A shows the cooled portion, and FIG. 6B the non-cooled portion, of the output electronics circuitry which begins with the detector.

FIG. 6A shows diagrammatically the cooled first stage of the pre-amplifier, i.e., the circuitry carried by circuit board 64 inside Dewar 60. The photo-detector 50 is connected by conductors 70 and 72, respectively, to gates 74 and 76 of two junction field effect transistors 78 and 80, which constitute a differential amplifier. The sources of transistors 78 and 80 are both connected by line 82 to a negative reference voltage (see FIG. 6B).

Figure 6B:
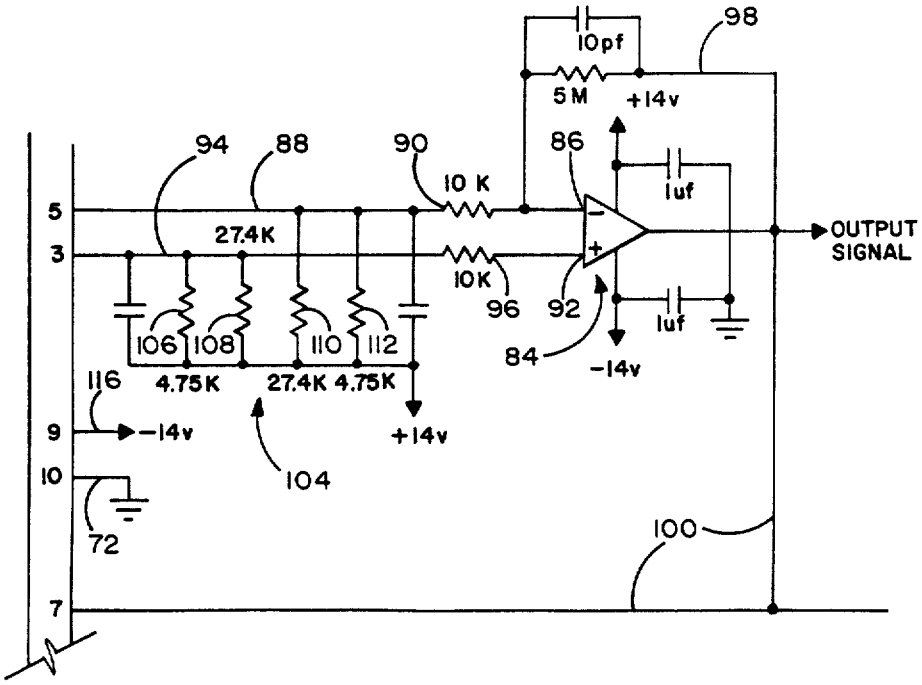

FIG. 6B shows diagrammatically the warm, or non-cooled, second stage of the pre-amplifier, i.e., the portion of the pre-amplifier circuitry not located in Dewar 60. The second stage of the pre-amplifier has an operational amplifier 84, whose first input 86 is connected by a conductor 88 through a resistor 90 to the drain of junction FET 80 (FIG. 6A), and whose second input 92 is connected by a conductor 94 through a resistor 96 to the drain of junction FET 78 (FIG. 6A). A feedback loop 98 connects the output of op amp 84 to its input 86. A pre-amplifier feedback loop is provided by a conductor 100 which connects the output of op amp 84 to the germanium photo-diode 50 (FIG. 6).

The feedback conductor 100 includes a very high value resistor 102. A satisfactory value of this resistor has proved to be 1 gigohm. Experience has shown that the primary noise problem at the pre-amplifier is the "Johnson" noise of the feedback resistor. A high resistor value, therefore, has the effect of improving the signal-to-noise ratio when this resistor is cooled to ~77° K.

A resistance network 104 in FIG. 6B has the effect of setting the gain of the first, or input, stage of the pre-amplifier, thus establishing the ratio of the gains in its first and second stages. Resistors 106 and 108 are connected in parallel between the positive reference voltage and conductor 94; and resistors 110 and 112 are connected in parallel between the positive reference voltage and conductor 88. The source of the JFETS 78 and 80 are connected through a resistance 114 and a conductor 116 to the negative reference voltage. The conductor 72, which is connected to photo-diode 50 and to the gate of JFET 80, is connected to ground (FIG. 6B). The values of the resistors and capacitors provide an example of a successful pre-amplifier in the disclosed system; but various other circuit designs could be substituted. The transistors which constitute op amp 84 are preferably bi-polar transistors.

As is apparent, the cooled first stage of the pre-amplifier shown in FIG. 6A provides a voltage amplification; and the non-cooled second stage shown in FIG. 6B provides a further voltage signal amplification. The overall feedback loop provides a current-in, voltage-out characteristic.

As previously stated, the germanium photo-detector has the advantage of compactness. Thus the size of Dewar 60 need only be a small fraction of the size of a Dewar enclosing a PM tube. The tube has the additional disadvantage that it must be maintained at all times at an awkward intermediate temperature, whereas the germanium photo-diode works well at the liquid nitrogen temperature (77° K.).

FIG. 3 shows a MIDAC high-performance interferometer which has proved to have the accuracy required for use in the short wavelength region of interest in the present application. Its main beamsplitter 40a receives the incoming beam 28a, reflects part of the radiation along one arm toward a fixed mirror 42a, and transmits the remaining radiation along the other arm toward a movable "scanning" mirror 44a.

The high accuracy of the interferometer depends largely on the alignment and balancing of movable mirror 44a, which is mounted on the front of a movable carrier 120. Carrier 120 is supported at opposite sides of its axis of motion by two air bearings 122 and 124, each of which is supported on, and guided by, a rod 126 extending parallel to the axis of motion. The use of two air bearings, as opposed to one, prevents the movable structure from rotating about its roll axis. A linear actuator 128 drives the movable structure in a reciprocating mode.

The center of gravity of the movable structure must coincide with the fore-and-aft "center of pressure", or "center of support", of the air bearings, in order to avoid any "tipping" deviation of the path of the moving mirror. In order to properly locate the center of gravity of the moving structure, a weight 130 has, in experimental embodiments, been attached to the movable structure. The inherent lateral stability of the interferometer prevents any lateral, or "yawing", deviation of the path of the movable mirror, even though the center of gravity of the movable structure may be displaced slightly from the center of pressure (or center of support) of the air bearings. For example, a movable mirror 132, which is part of the "white" light interferometer used to start each scan, is carried by the movable structure at one side of the movable mirror 44a; and its weight does not require lateral balancing.

The primary radiation beams reflected by mirrors 42a and 44a are recombined at beamsplitter 40a; and the recombined beam 46a exits the interferometer toward the detector.

As previously stated, the interferometer has, in effect, three radiation sub-systems. In addition to the basic analytical radiation system, which has been described, it has a "white-light" scan-starting radiation sub-system, and a laser sub-system which provides a clock to control data sampling frequency. As shown in FIG. 3, the white light system comprises a source 134; a beamsplitter 136; a fixed mirror 138 at the end of one interferometer arm; the previously-mentioned movable mirror 132, which is mounted on the same carrier 120 as movable mirror 44a; and a white light detector 140. This independent white light interferometer beam is so arranged as to have its zero path difference point peak offset from the zero path difference point peak of the analytical beam, so that it provides a suitable, and identical, starting point for successive analytical scans.

The laser clock-providing sub-system in FIG. 3 includes a helium neon laser generator 142; a mirror 144 which directs the laser beam along the center of the analytical beam; and a laser detector 146. The laser beam utilizes the same beamsplitter 40a, fixed mirror 42a, and movable mirror 44a, as the analytical beam. This placement of the laser beam in the center of the main analytical aperture renders the interferometer insensitive to several potential error sources.

For a more detailed description of the interferometer shown in FIG. 3, reference may be had to Auth U.S. application Ser. No. 297,547, filed Aug. 31, 1981.

It has previously been explained that use of an interferometer in a PL system for short wavelength sample-emitted radiation, while it has proved to have outstanding benefits, does require various protective measures to be used. As already stated, these measures include holding to much tighter interferometer performance specifications that a normal interferometer use requires. Another important measure is blocking from the detector 50, to the maximum extent feasible, all radiation not provided by photons from the sample.

The MIDAC interferometer, comprising the features discussed above, has proved capable of maintaining the necessary performance tolerance, which is approximately twice as stringent as the tolerance permissible in interferometers in normal use.

The blocking of all light except the sample-emitted photons includes several expedients. As previously stated, the argon ion laser 18 (FIG. 2), which supplies excitation radiation to the sample, is both shrouded and filtered. The helium neon laser 142 (FIG. 3), which provides interferometer clock pulses to control data sampling, is also shrouded and filtered. It is enclosed in a metal container (as shown), and has a filter 148 blocking undesired plasma lines.

The white light, used in the sub-subsystem which determines the starting point of the analytical scan, is automatically turned off during the analytical scan. The timing diagram is shown in FIG. 7. The top horizontal segment A of FIG. 7 shows the change in position of movable mirror 44a from "start of scan limit" (SOSL) to "end of scan limit" (EOSL). Movement of the mirror in the scanning direction is gradual, as shown, whereas return of the mirror to its original position is relatively rapid. The next horizontal segment B shows the forward driving pulse which moves the motor in the scanning direction. Horizontal segment C includes vertical arrows representing the points at which the white light interferometer has zero path difference in its two arms, i.e., its peak output point. Horizontal segment D shows the on and off periods of the white light. The white light is automatically turned on at the beginning of the return stroke of the movable mirror. It is automatically turned off at the next clock signal after its peak output point. Horizontal segment E shows the data taking periods, which begin one clock pulse after the white light is turned off, and end when the forward stroke of the movable mirror ends. As previously stated, the effect of each white light peak is to determine at which clock pulse the analytical data taking will begin. Horizontal segment F includes vertical arrows representing points at which the analytical interferometer has zero path difference in its two arms.

The means for switching on and off the white light is included diagrammatically in FIG. 2, in which data system 56 is shown controlling an electronic switch 152 which turns on and off the white light source 134. The white light is directed by beamsplitter 136 to fixed mirror 138 and movable mirror 132; and the recombined beam is received by white light detector 140. The detector output is amplified at 154 and its signal is directed into the interferometer electronic control system.

The remaining source of undesired radiation is ambient light. As shown in FIG. 5, a filter 156 covering the window in Dewar 60 can be used to filter out radiation wavelengths below approximately 0.8 microns.

FIG. 8 shows a metal cover 158 enclosing the entire FTPL analytical system, including the PL input portion, the interferometer portion, and the detector output portion. The primary function of the cover 158 is to minimize the effect of ambient atmospheric changes on the analytical system. But it also has the advantage of blocking out ambient light.

Figure 1:
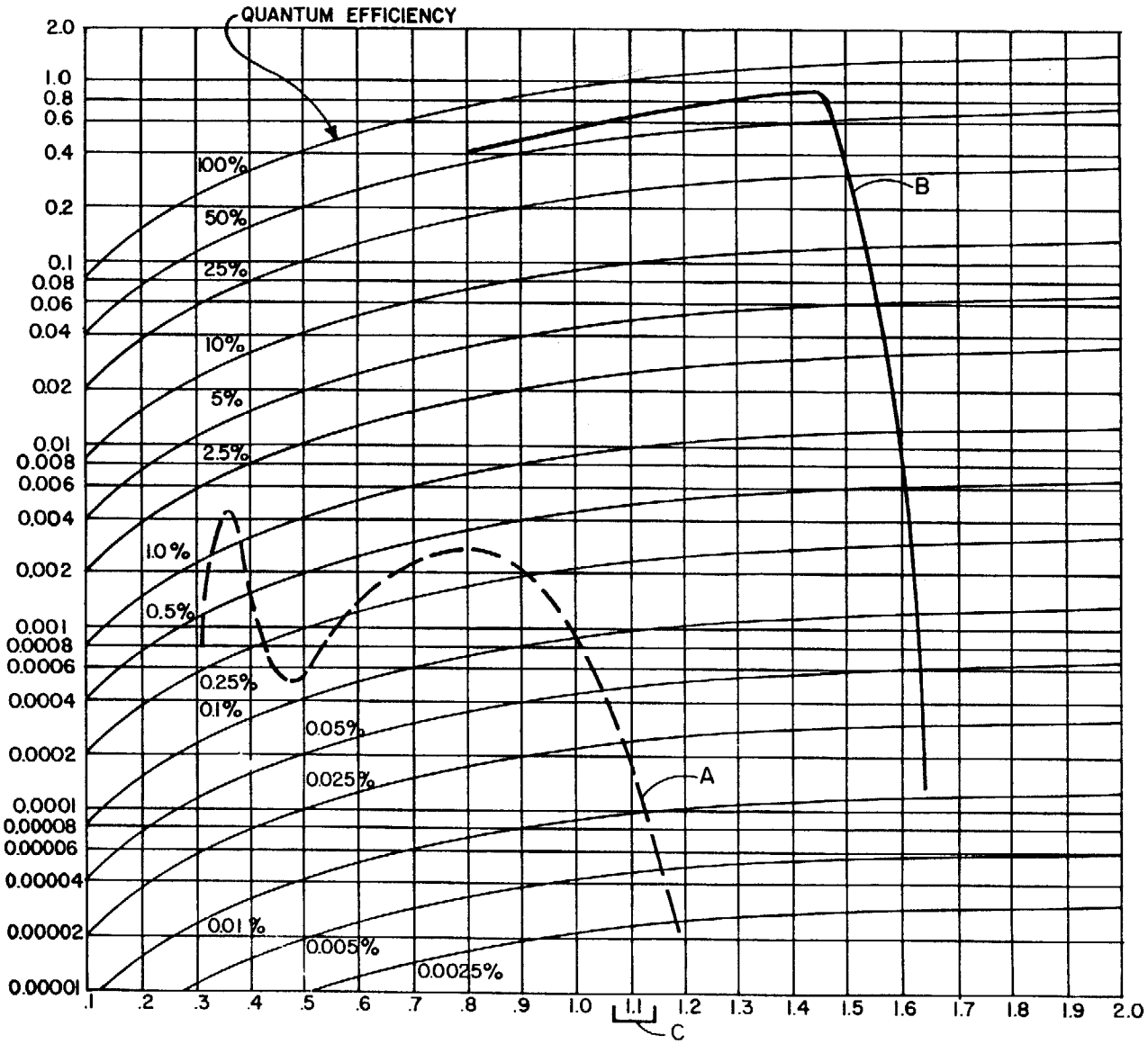
FIG. 1 is a graph comparing the spectral response curves of a typical photo-multiplier tube and a typical germanium photo-diode.

FIG. 1 shows the significant wavelength range advantage of the germanium photo-detector over the photo-multiplier tube. The X-axis scale is radiation wavelength in microns. The Y-axis scale is a log scale representing response of the detectors in amperes per watt. The response of the S1 tube is illustrated by the dashed line A; and the response of the germanium photo-detector is illustrated by the solid line B. The much higher response level of the photo-detector is not its primary advantage, because it lacks the internal amplification provided by the tube.

However, the micron range comparison is very significant. The horizontally-extending bracket C, shown on the X-axis, represents the region of primary interest in PL analysis of silicon surfaces. (In the specification the range of primary interest is indicated to be approximately 1.07 through 1.127 microns). It is apparent from the FIG. 1 graph that the response from the PM tube has dropped drastically at the 1.1 micron wavelength, where the silicon luminescence occurs. On the other hand, the response of the germanium photo-detector remains consistently high, and substantially level, from about 0.8 to over 1.4 micron wavelengths.

Figure 4A:
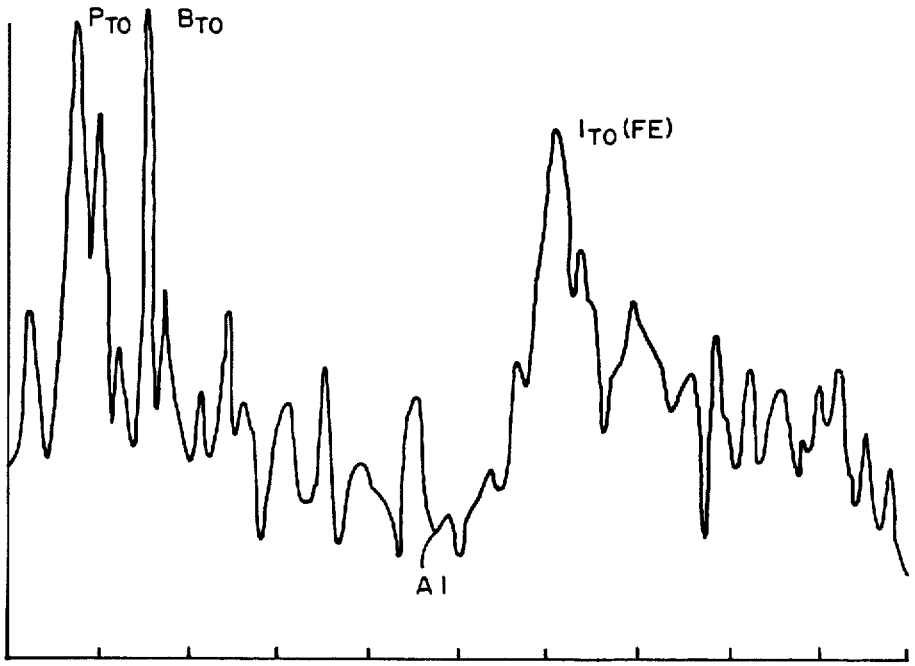
FIGS. 4A and 4B provide graphic comparisons of spectral information from the FTPL analysis apparatus of the present invention with spectral information from prior PL analysis apparatus.
Figure 4B:
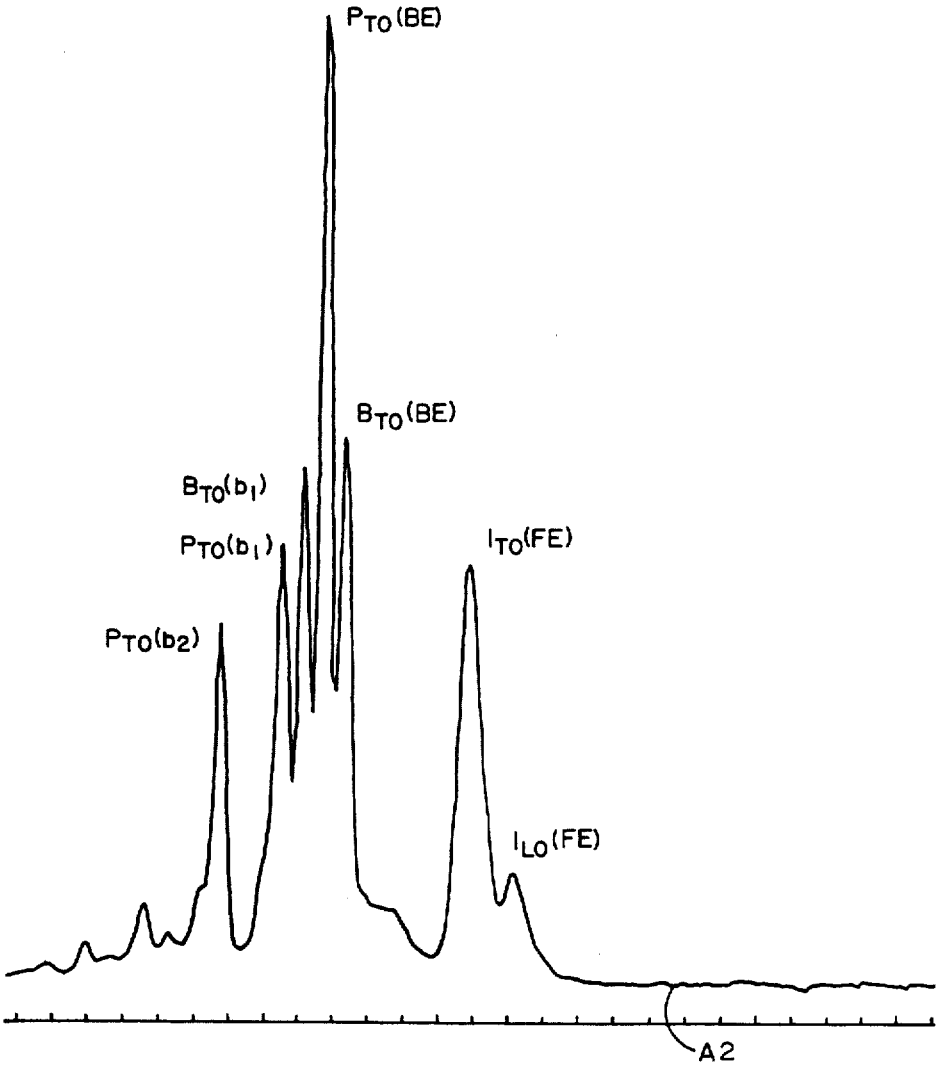

A comparison of the present FTPL system with a previous PL silicon surface analytical system is illustrated by FIGS. 4A and 4B. FIG. 4A shows a spectrograph produced by the PL analysis system of Application Ser. No. 411,603. FIG. 4B shows a spectrograph produced by the FTPL analysis system disclosed in this application. The radically reduced noise level using the present invention is readily apparent from the base (lower) lines A1 in FIG. 4A and A2 in FIG. 4B.

In FIGS. 4A and 4B the wavelength values are plotted on the X-axis, with decreasing wavelengths (higher frequencies) from left to right. In each figure, the intrinsic signal is marked $I_{TO}$ (FE), which signifies "intrinsic", "transverse optical", and "free exciton". The line marked $B_{TO}$ on each figure represents boron, and the line marked $P_{TO}$ on each figure represents phosphorous. The B and P lines are "bound exciton" lines. The fact that the B and P lines on FIG. 4B are much clearer and more pronounced than the B and P lines on FIG. 4A evidences the remarkable benefits of the present invention. Furthermore, the absence of "clutter" in FIG. 4B permits identification of three additional lines, two phosphorous ($P_{TO}b_1$, and $P_{TO}b_2$) and one boron ($B_{TO}b_1$).

Figure 9A:
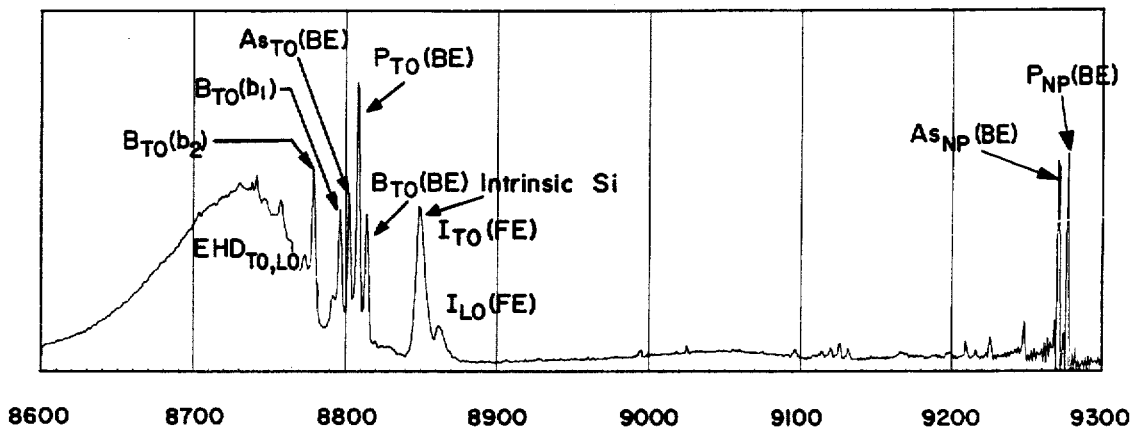
FIGS. 9A–9E are a series of FTPL spectra based on the same sample, but with varying laser excitation intensities on the sample, the purpose being to illustrate control of the EHD phenomenon.
Figure 9B:
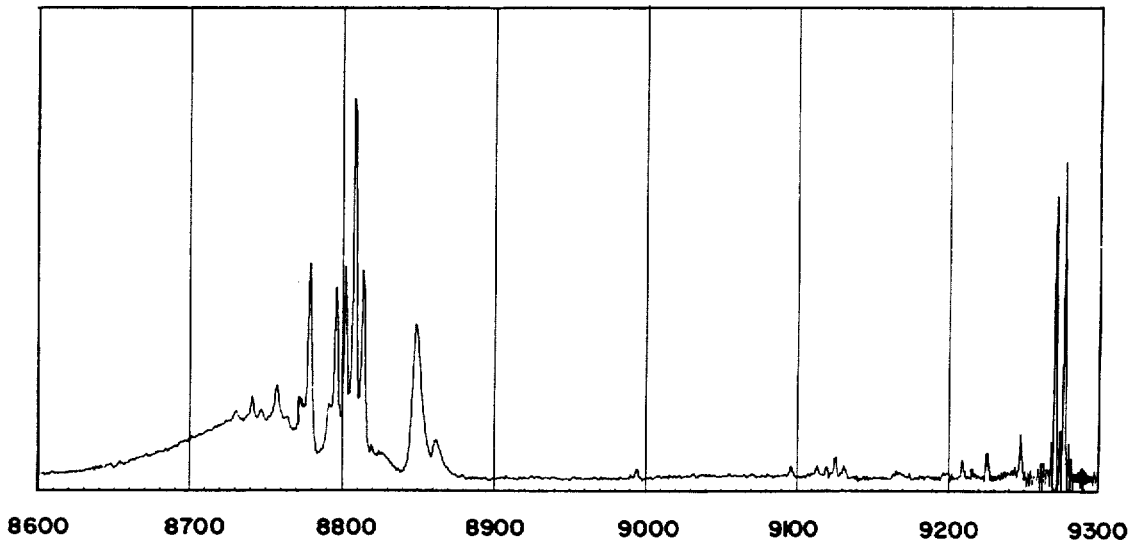
Figure 9C:
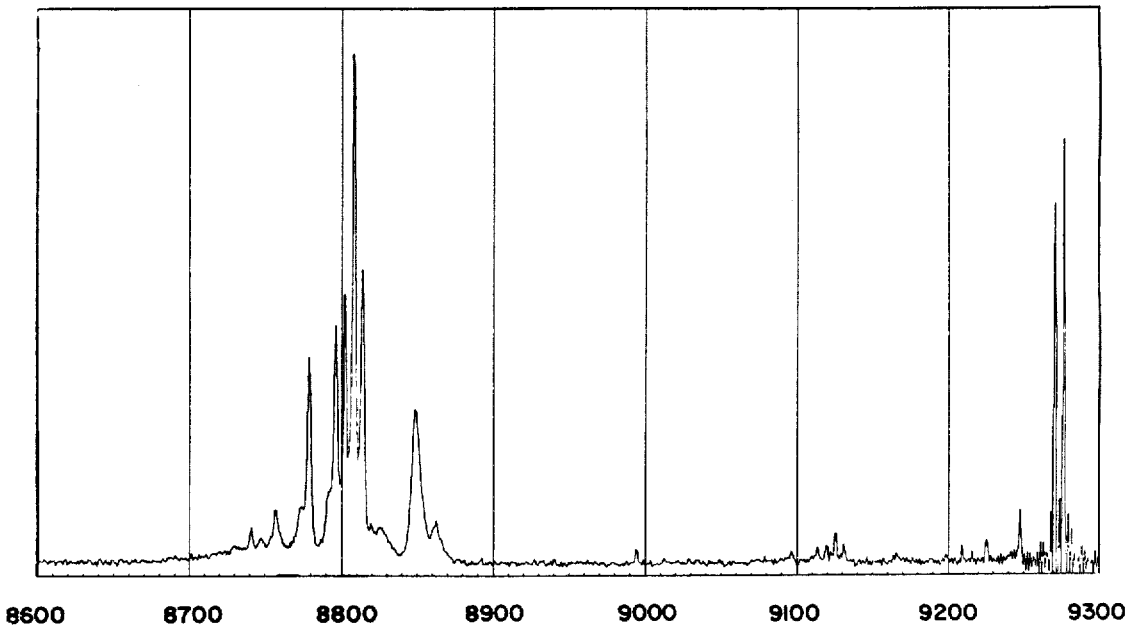
Figure 9D:
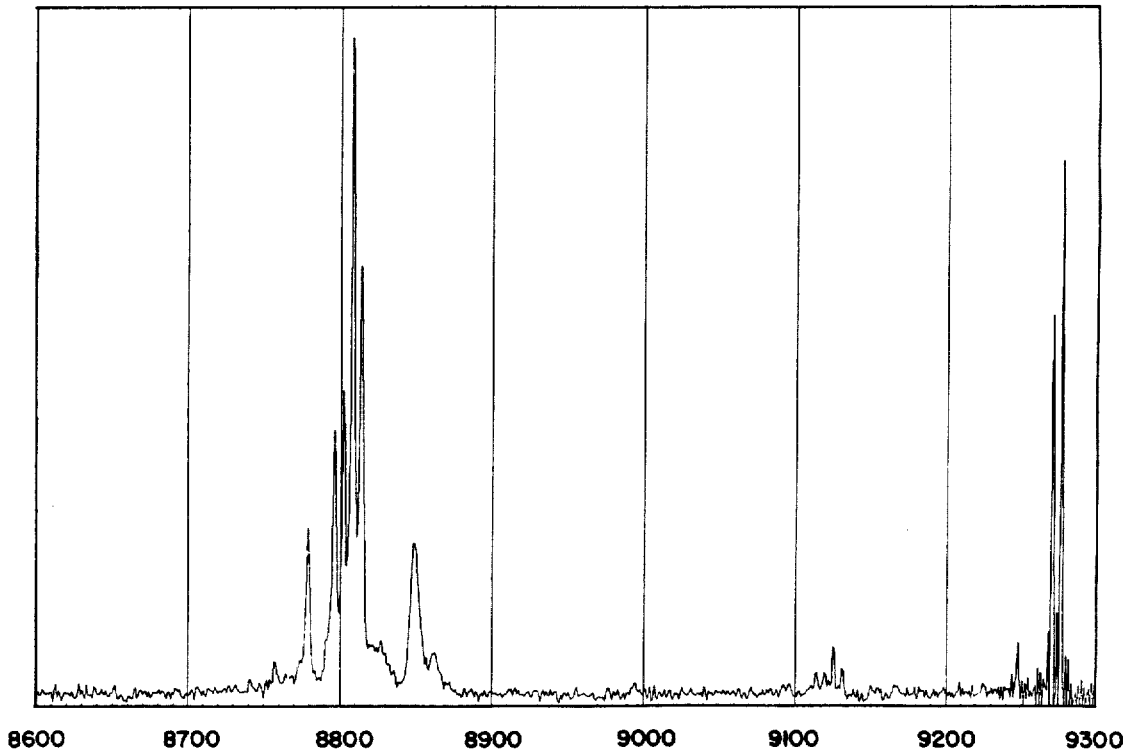
Figure 9E:
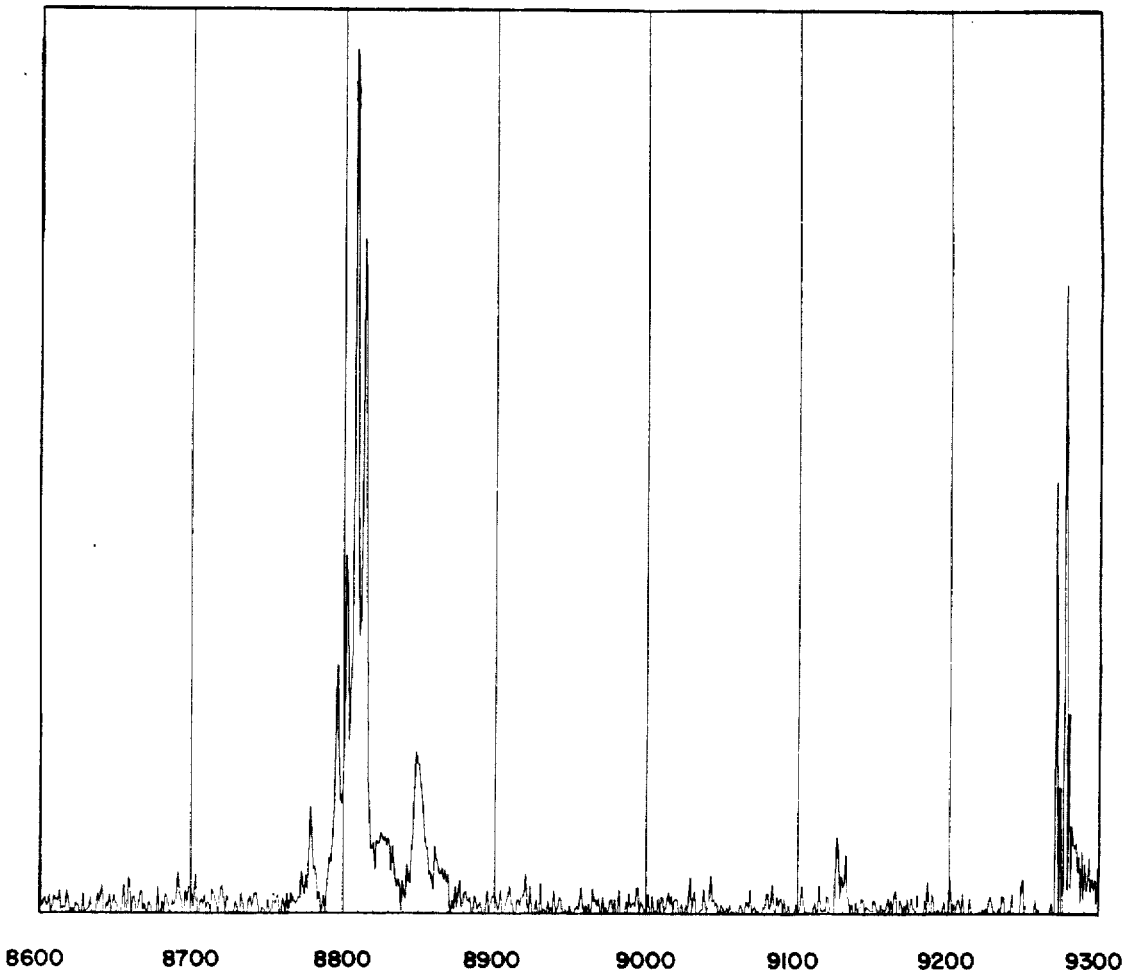

Subsequent spectrographs produced with the FTPL system of the present invention are shown in FIGS. 9A through 9E, each from the same sample, but using a different power of the laser beam directed onto the sample. FIG. 9A was produced with a laser power of 100 mW; FIG. 9B with a laser power of 50 mW; FIG. 9C with a laser power of 25 mW; FIG. 9D with a laser power of 12 mW; and FIG. 9E with a laser power of 6 mW. All of the figures 9A through 9E have a resolution of 2.0 $cm^{-1}$.

The purpose of the two series of FIGS. 9A through 9E, and 10A through 10E, is primarily to show the dramatic difference obtained by reducing the formation of electron-hole droplets (EHD) in the semiconductor crystal. Reduction in laser beam power tends to reduce EHD formation, thereby providing better calibrated data. Reduction in laser beam power is possible because of the tremendous sensitivity advantage provided by the present invention.

The significance of the EHD effect relates to the complex dynamics of the excitonic matter in silicon. One of the important parameters in PL analysis is the exciton gas density. This exciton gas density is a function of the excitation power incident upon the sample, the impurity concentration levels in the sample, the type of impurity present, and the crystal structure defects present. The EHD formation occurs above a threshold exciton gas density. Dramatic variations of EHD formation levels from sample to sample for a given laser excitation level have been observed. This EHD variation indicates that the exciton gas density is varying from sample to sample; and the resulting change in excitonic gas density also varies the relative intensities of the free exciton and bound exciton luminescence features. Also, the EHD interacts with the bound excitons in a manner not clearly understood. Since the quantitative measurement of impurity concentration is calculated from these relative intensities, the changing excitonic gas density effectively tends to destroy the calibration of the measurement.

In each of FIGS. 9A through 9E, the data is so plotted as to keep the height of the intrinsic (free exciton-$I_{TO}$) signal approximately the same. The effect of the EHD phenomenon can be observed in two ways. (1) The "hill" A at the lower left of each figure represents the EHD volume. Its size is particularly large in FIG. 9A; and it decreases in each successive figure until it substantially disappears from FIGS. 9C, 9D and 9E. This disappearance of "hill" A indicates that the formation of EHD has been stabilized. (2) As the EHD volume is reduced by reducing the laser beam power from figure to figure, the height of the bound exciton signals, such as $P_{TO}$ (phosphorous) and $B_{TO}$ (boron), increases dramatically. Since the determination of impurity concentrations is based on the ratio of the bound exciton signals to the free exciton signals, clearly the difference in results is highly significant.

The absolute value of the ratio of bound excitons to free excitons is not the crucial factor in calibration. But the consistency of performance of the PL system from sample to sample is crucial. Therefore, the object of testing the same sample at varied laser power ratings is to determine at what power rating the EHD phenomenon becomes stabilized and therefore negligible. The maximum power at which this occurs will provide the optimum test results for that sample. This optimum power level should be redetermined for each sample. Calibration will thus be enhanced by using a method of varying the laser power until the EHD effect has substantially stabilized in the data output, and then taking the desired data at this optimum laser power.

Based on the series of spectra shown in FIGS. 9A-9E, the preferred excitation level for the sample appears to be 25 mW, which produces the spectrum of FIG. 9C. The reasons for this preference are that: (a) the EHD phenomenon has substantially disappeared with laser intensity reduction to 25 mW; and (b) the signal-to-noise ratio is better at this laser intensity than at lower intensities.

Figure 10A:
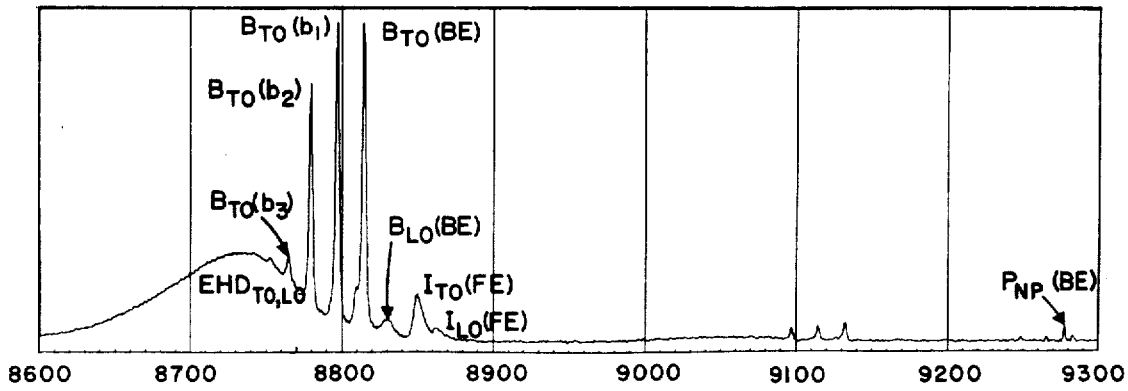
FIGS. 10A–10E are a series of FTPL spectra showing data similar to that shown in FIGS. 9A–9E, but based on a different sample.
Figure 10B:
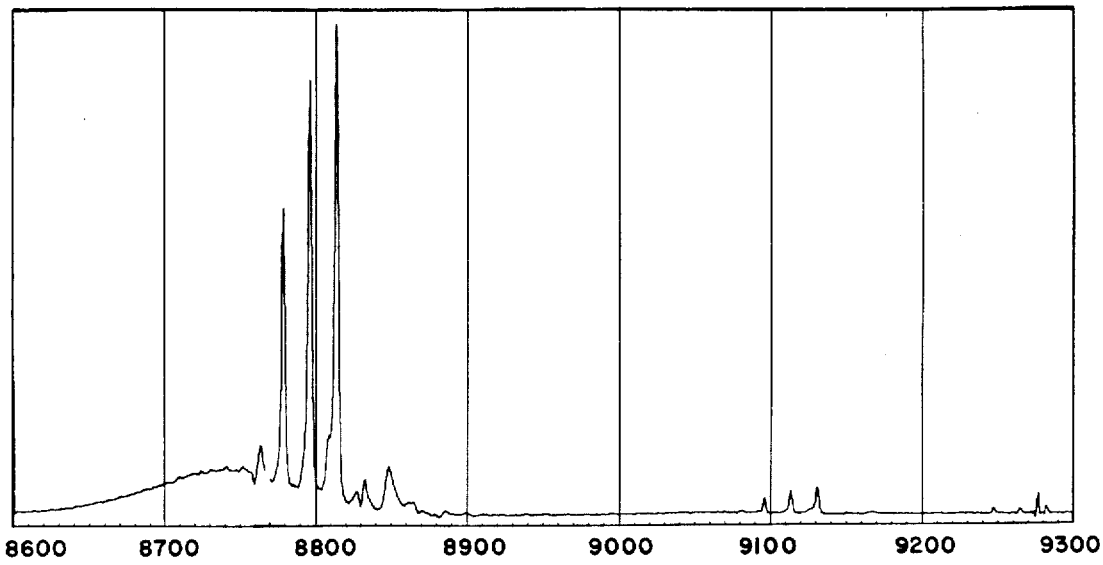
Figure 10C:
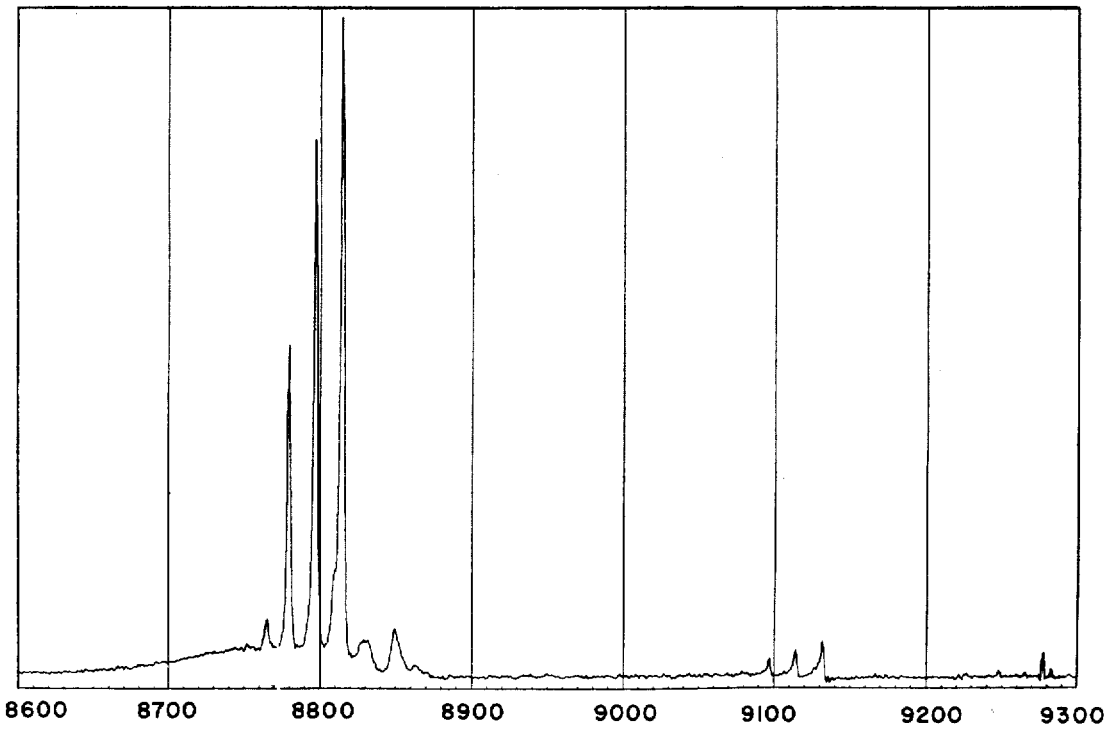
Figure 10D:
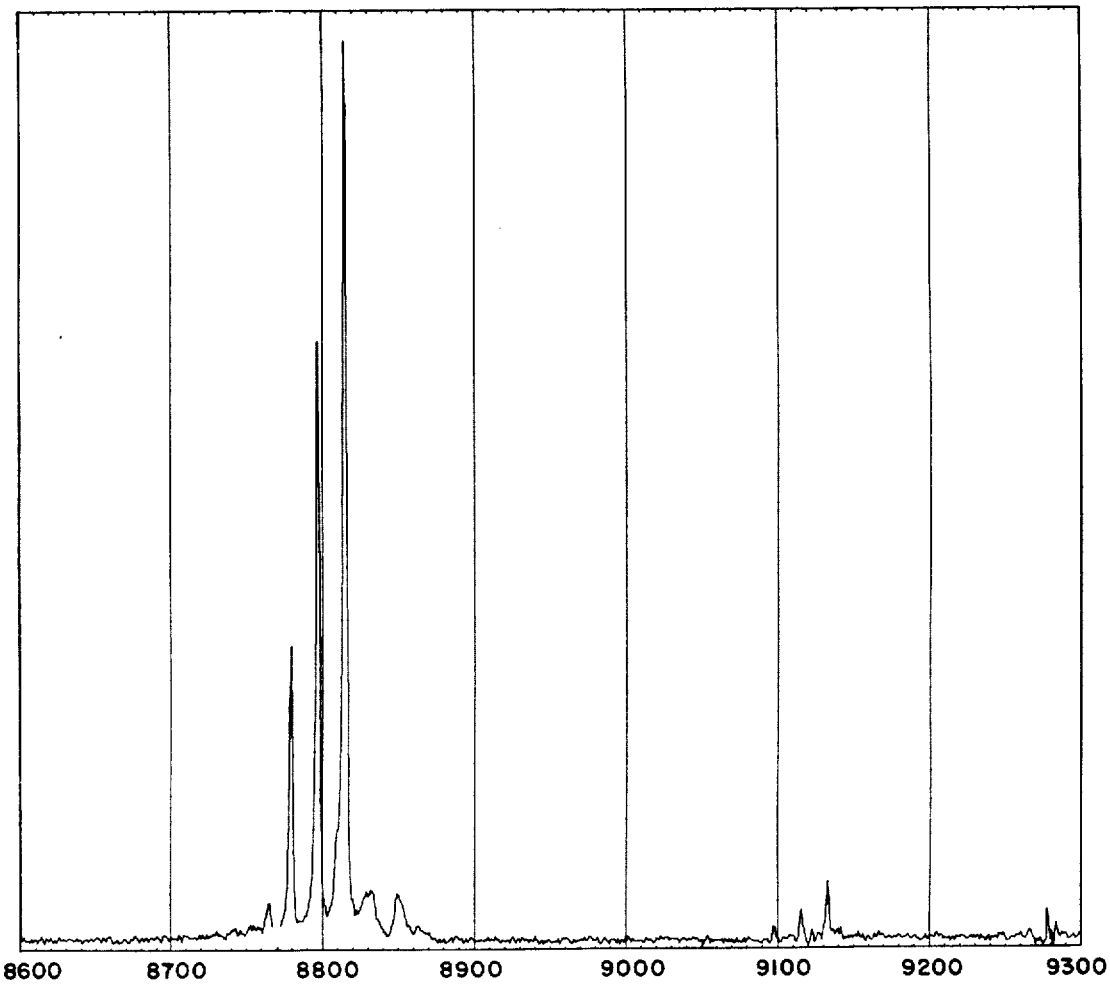
Figure 10E:
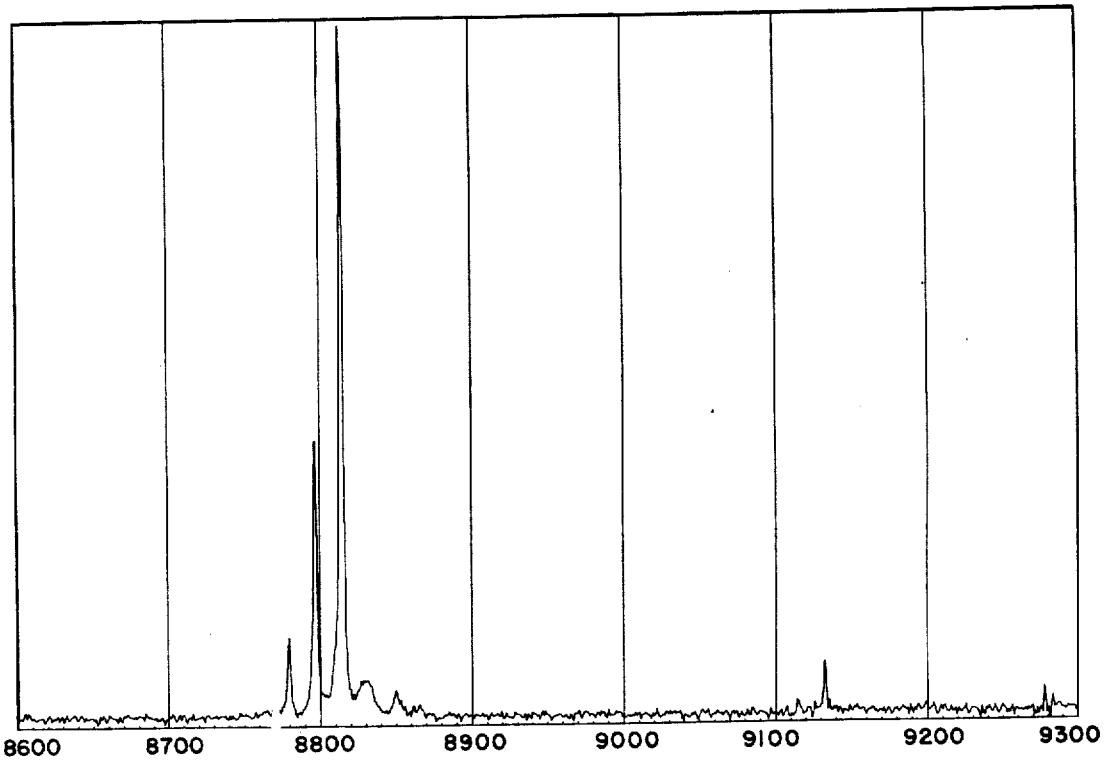

FIGS. 10A-10E show the effect of laser intensity reduction on the EHD phenomenon in a different sample. The respective laser intensity values are: in FIG. 10A-50 mW; in FIG. 10B-25 mW; in FIG. 10C-12 mW; in FIG. 10D-6 mW; and in FIG. 10E-3 mW. The EHD effect, shown by hill A at the lower left of each figure, is pronounced in FIG. 10A (at 50 mW), substantially reduced in FIG. 10B (at 25 mW), further reduced in FIG. 10C (at 12 mW), and essentially disappears in FIGS. 10D and 10E. In keeping with the practice of analyzing the sample at the highest laser intensity which has stable (optimal) EHD effect, the preferred intensity level for this sample would be 6 mW (FIG. 10D).

The tremendous sensitivity advantage provided by the present invention permits rapid collection of many spectra at varying excitation intensities, from which the optimal excitation level (usually very low) for a given sample can be found. This simple procedure can be performed for each sample measured, thus constraining an important variable in the measurement: excitonic gas density. The ability to obtain sharp spectrographs at radically reduced laser power levels demonstrates the dramatic improvement in sensitivity over previous monochromator-based systems.

The spectacular performance differences between the FTPL system of the present invention and the prior art can be illustrated by comparing it to a typical monochromator-based (M-B) system which is currently in use. The M-B system spends approximately 20 minutes per spectrum, and looks at only a very small portion of the spectrum for each sample. Its sensitivity is marginal. By contrast, the FTPL system provides four times greater resolution, data acquisition in three to six minutes, and sensitivity (signal-to-noise ratio) approximately two orders of magnitude better. Combining these three values provides an overall system performance improvement of at least three orders of magnitude. Furthermore, the spectral coverage is approximately two orders of magnitude wider.

In other words, impressive improvements have been obtained simultaneously in all major features—sensitivity, resolution, spectral coverage, and speed of data acquisition. This means that trade-offs necessary in monochromator PL systems are essentially unnecessary with the present invention.

With monochromators, the resolution is a function of the entrance and exit slit widths; the smaller the slits, the narrower the resolution. Unfortunately, the throughput is also a function of the slits. As the slit width decreases, so does the amount of light getting through the monochromator. This means that improved resolution requires sacrificing optical throughput, and hence either signal-to-noise or data collection time, or both. The present FTPL improves the tradeoff situation immensely because of the way an interferometer manages higher resolution. In the constant [throughout] *throughput* mode of operation the beam aperture need not be varied for the higher resolution scans; it is only necessary to move the mirror farther, thus increasing the amount of the interferogram information obtained.

Adequate resolution is important to resolve the narrowly spaced "no-phonon replica" features which appear at the high frequency end of the spectrum. This is readily accomplished with the FTPL of the present invention.

Among the accomplishments of the FTPL are:

(a) Discovery of several new luminescence line groups associated with different types of defects or impurities in silicon samples, heretofore unmentioned in the literature.

(b) Enhanced understanding of the extent of the excitation intensity dependence of the luminescence lines of interest in silicon.

(c) Learning much about the competitive nature of the different impurities in silicon, important for the advancement of quantitative analysis of impurity concentrations in silicon.

(d) Improving dramatically the lower concentration detection limits for the dopant impurities with the FTPL's enhanced sensitivity.

(e) Improving dramatically the ability to unequivocally identify (particularly in the no-phonon region) the closely-spaced shallow impurity luminescence lines, with the FTPL's enhanced resolution capabilities.

Figure 11:
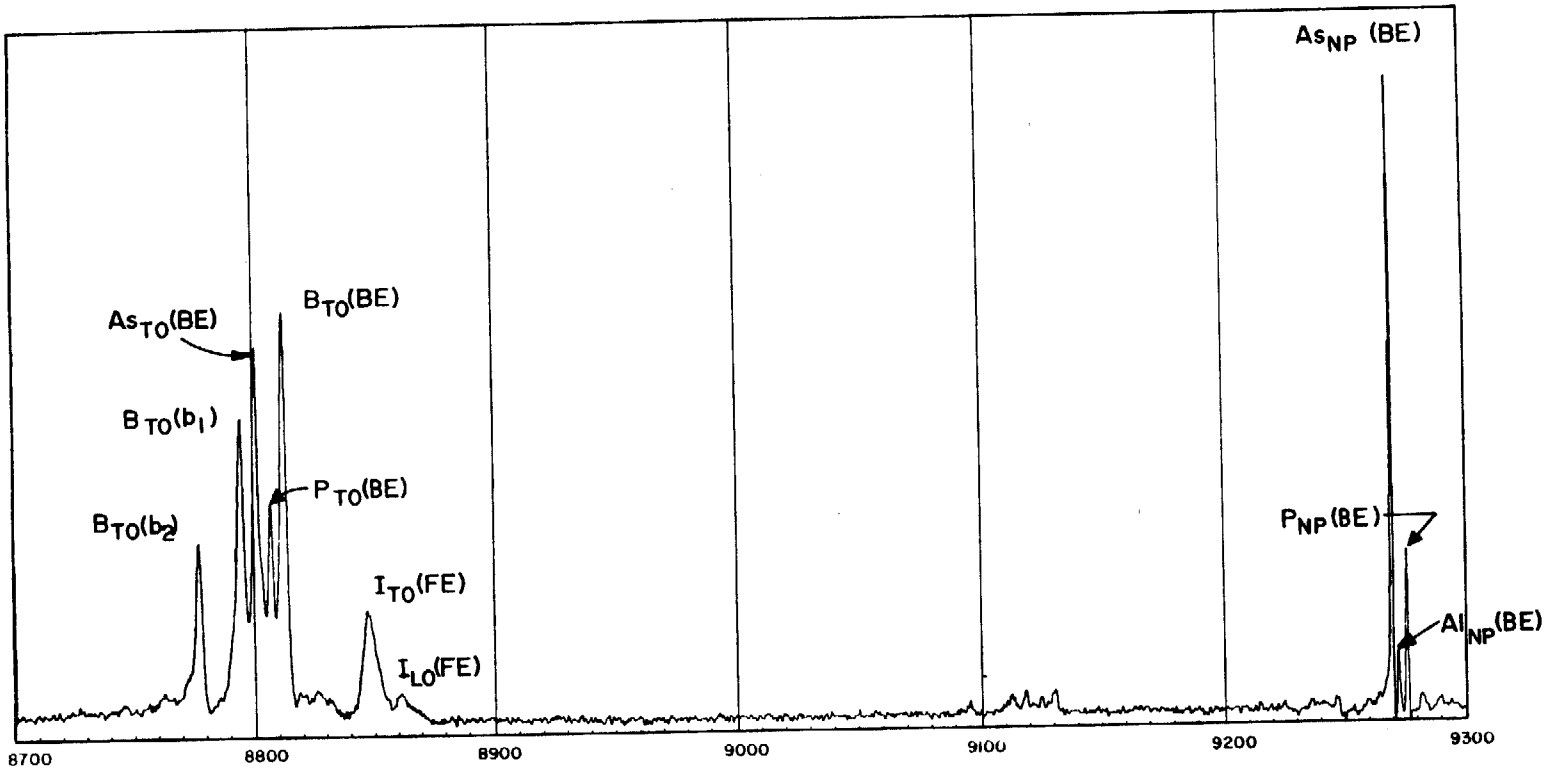
FIG. 11 shows a single FTPL spectrograph, which illustrates the benefits of an unusually fine resolution, coupled with high sensitivity and wide spectral scan.

The remaining figures further demonstrate the validity of the claims made for the present invention. FIG. 11 shows a single spectrograph which illustrates both the resolution power and the breadth of the spectrum scanned by the FTPL. The resolution in FIG. 11 is 56 units, having a per unit value of 0.01 $cm^{-1}$; and the laser power is 8 mW. In other words, the resolution is approximately one-half wave number, whereas the available resolution in monochromator PL systems is usually five wave numbers.

A particularly impressive result of this high resolution spectrograph is the data in the no-phonon region, which is at the far right of the figure. Three clearly distinct peaks are seen, representing (as marked) arsenic, aluminum, and phosphorous, respectively. The value of the data from the no-phonon region lies in the fact that it makes possible identification of one or more features which cannot be separated in the center region of the spectrograph (which shows broader features, and which fails to disclose the aluminum in this sample). One reason for the sharper available lines in the no-phonon region is that the recombination of the hole-electron pair does not involve a phonon.

Figure 12A:
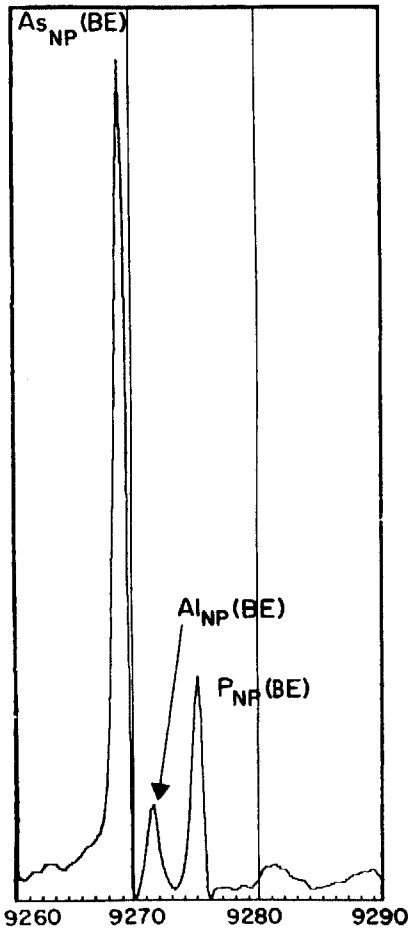
FIGS. 12A–12D use the same raw data as used in FIG. 11, but have progressively coarser resolution values, and are limited to the no-phonon region of the spectrum.
Figure 12B:
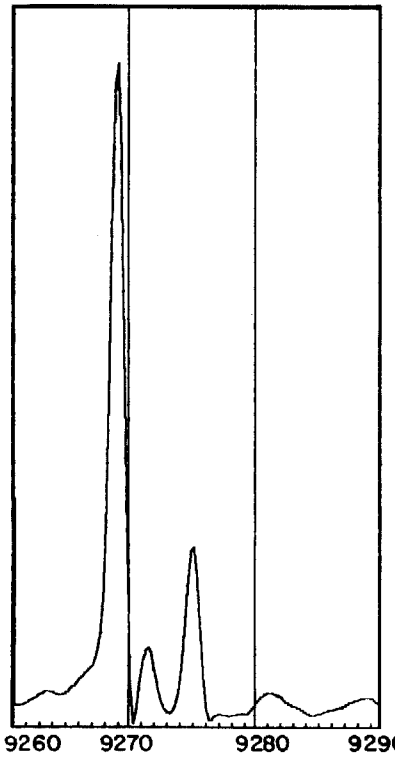
Figure 12C:
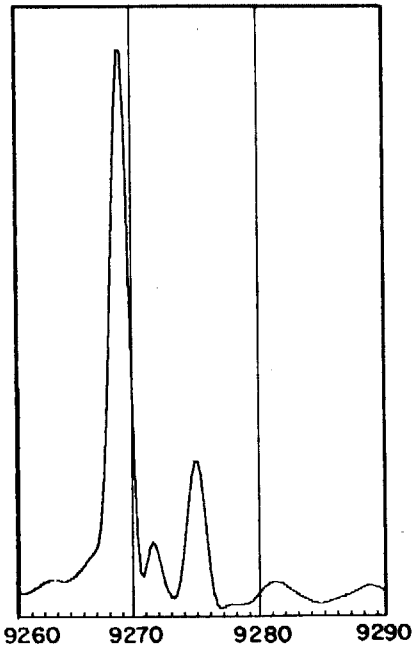
Figure 12D:
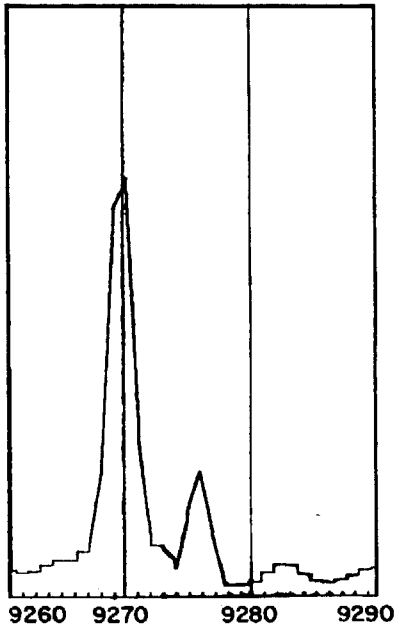

FIGS. 12A-12D use the same raw data as FIG. 11, but they show progressively coarser resolution values; and they show only the no-phonon region. FIG. 12A has a resolution of 0.56 $cm^{-1}$ (the same as FIG. 11); FIG. 12B has a resolution of 1.0 $cm^{-1}$; FIG. 12C has a resolution of 1.5 $cm^{-1}$; and FIG. 12D has a resolution of 2.0 $cm^{-1}$. As the fineness of resolution decreases, from that shown in FIG. 12A to that shown in FIG. 12D, the aluminum peak is gradually merged into the arsenic peak, and thus disappears. The general practice, using the FTPL system, is to obtain spectra both at 2 wave numbers ($cm^{-1}$) and at one-half wave number ($cm^{-1}$).

Figure 13A:
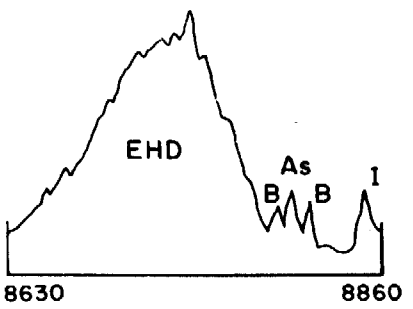
FIGS. 13A–13C are three monochromator based PL spectrographs, each showing a different portion of the spectrum.
Figure 13B:
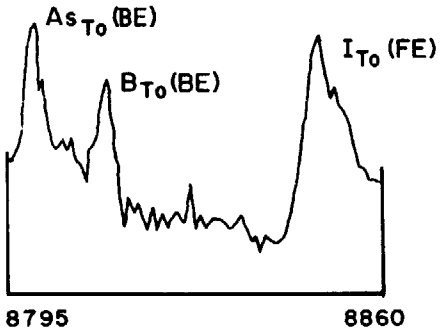
Figure 13C:
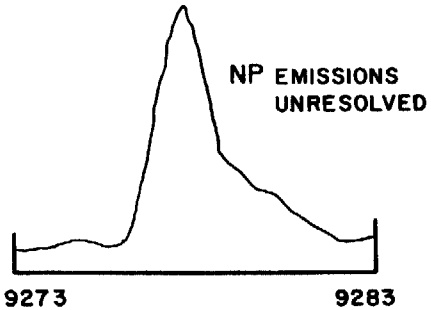

The same sample as that analyzed in FIGS. 11 and 12A-12D was also analyzed on a monochromator PL system, as shown in FIGS. 13A-13C, which are three separate spectrographs, each of which only shows a small portion of the spectrum covered by FIG. 11. FIG. 13A started at 8630 $cm^{-1}$, and had a step size of 5 Angstrom (distance between data points). FIG. 13B started at 8795 $cm^{-1}$, and had a smaller step size of 1 Angstrom. FIG. 13C started at 9273 $cm^{-1}$, and had a smaller step size of 0.5 Angstrom. FIG. 13C is in the no-phonon region. Even with its greatly reduced step size, and very small spectral width, it is unable to distinguish the three impurities which are clearly visible in FIG. 11.

Comparing FIGS. 13A-13C with FIG. 11 provides additional evidence of the magnitude of the advantages provided by the present invention. Not only is the difference in sensitivity dramatically illustrated; but also the single spectrograph of FIG. 11 provides extensive spectral data between and beyond the three spectrographs shown in FIGS. 13A-13C.

Figure 14A:
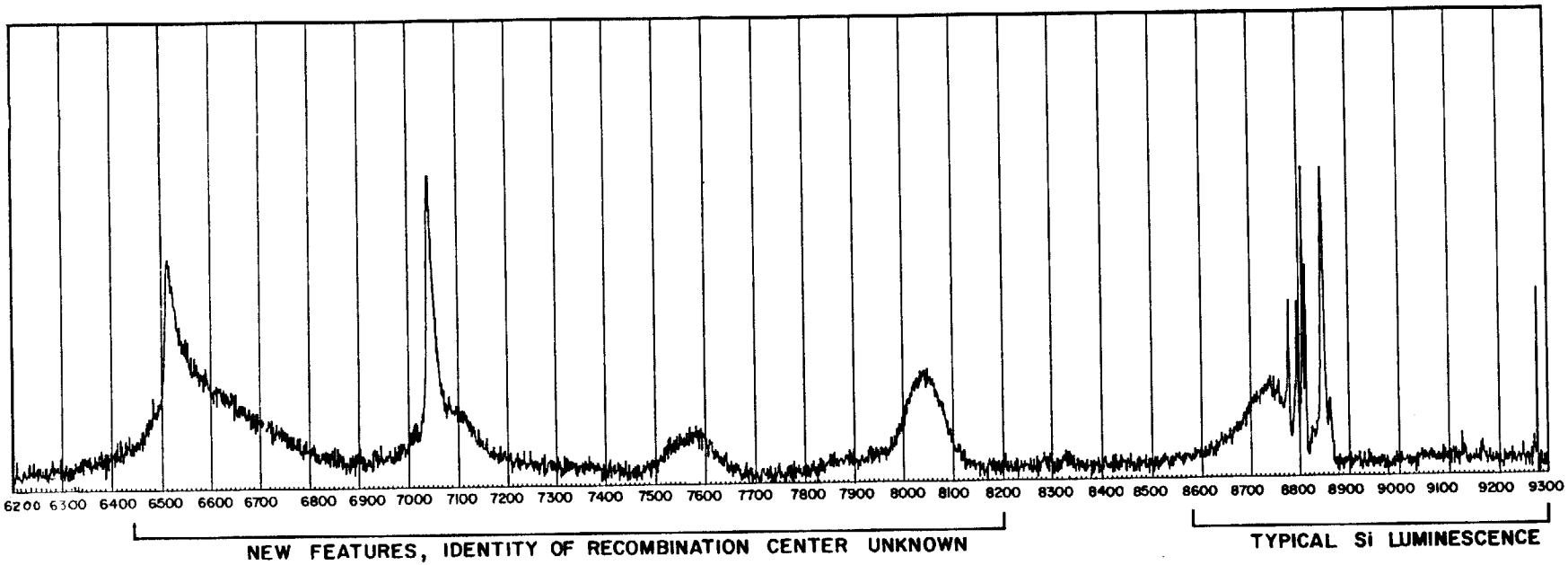
FIGS. 14A and 14B show spectrographs having new photoluminescence features discovered using the apparatus of the present invention.
Figure 14B:
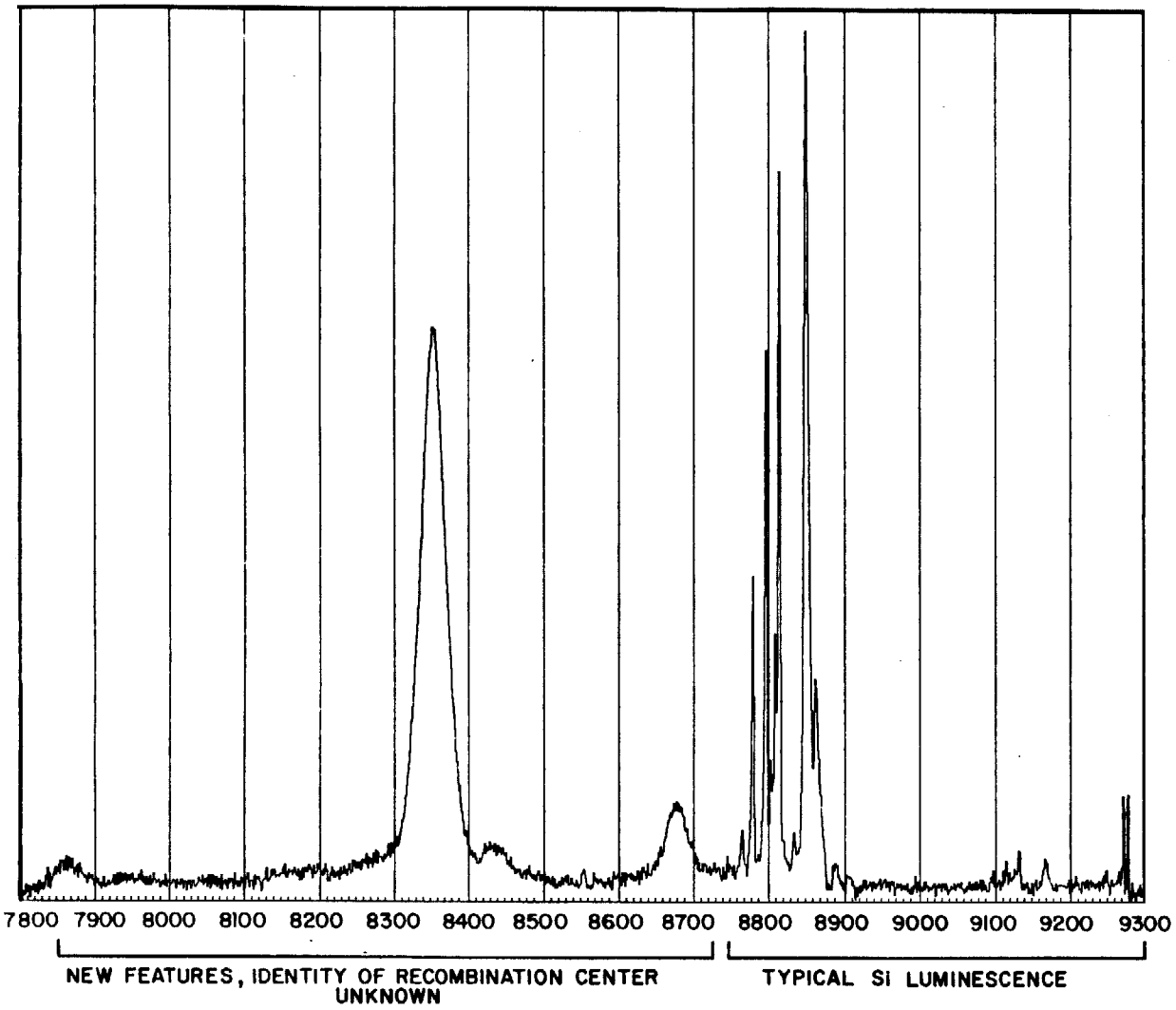

FIGS. 14A and 14B are of interest because they show that the present invention has recorded new photoluminescence features which were heretofore unreported in the literature, and were, therefore, presumably unobserved. FIG. 14A, showing data first observed on Jan. 17, 1984, indicates with arrows four new (previously unreported) photoluminescence features. FIG. 14B, showing data first observed on Apr. 6, 1984, indicates with arrows three new (previously unreported) photoluminescence features.

Figure 15A:
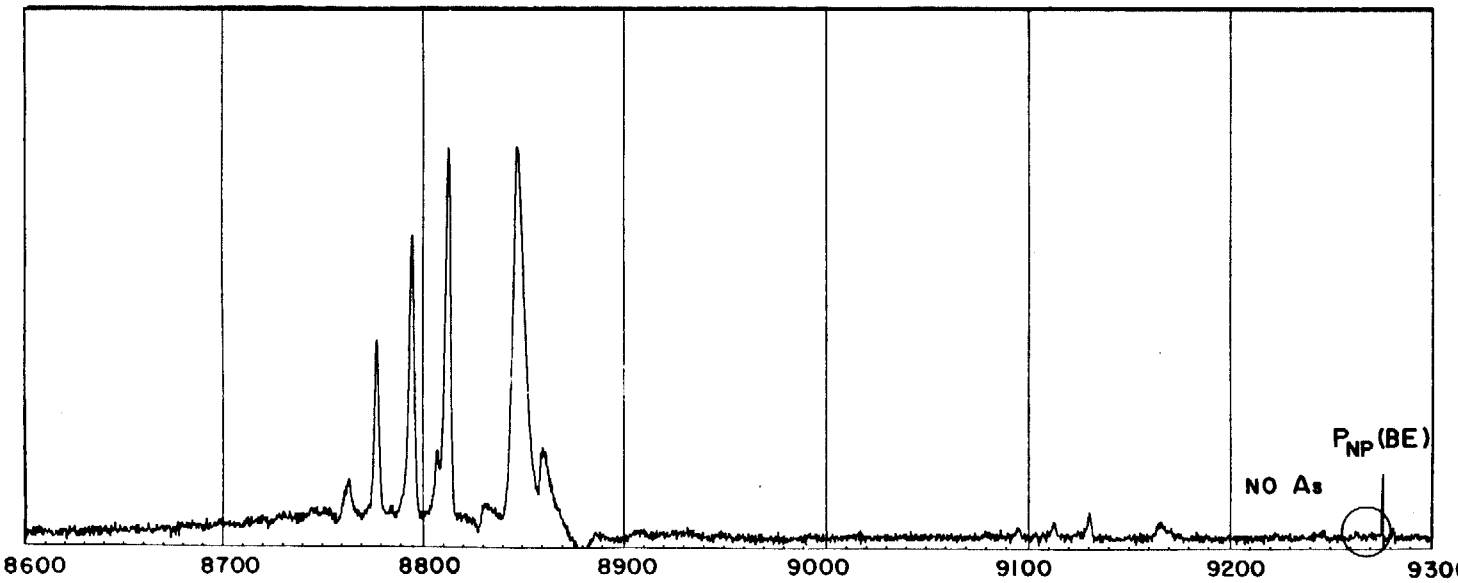
FIGS. 15A-15C are spectrographs illustrating the ability of the present invention to detect the "competitive" nature of different impurities.
Figures 15B, 15C:
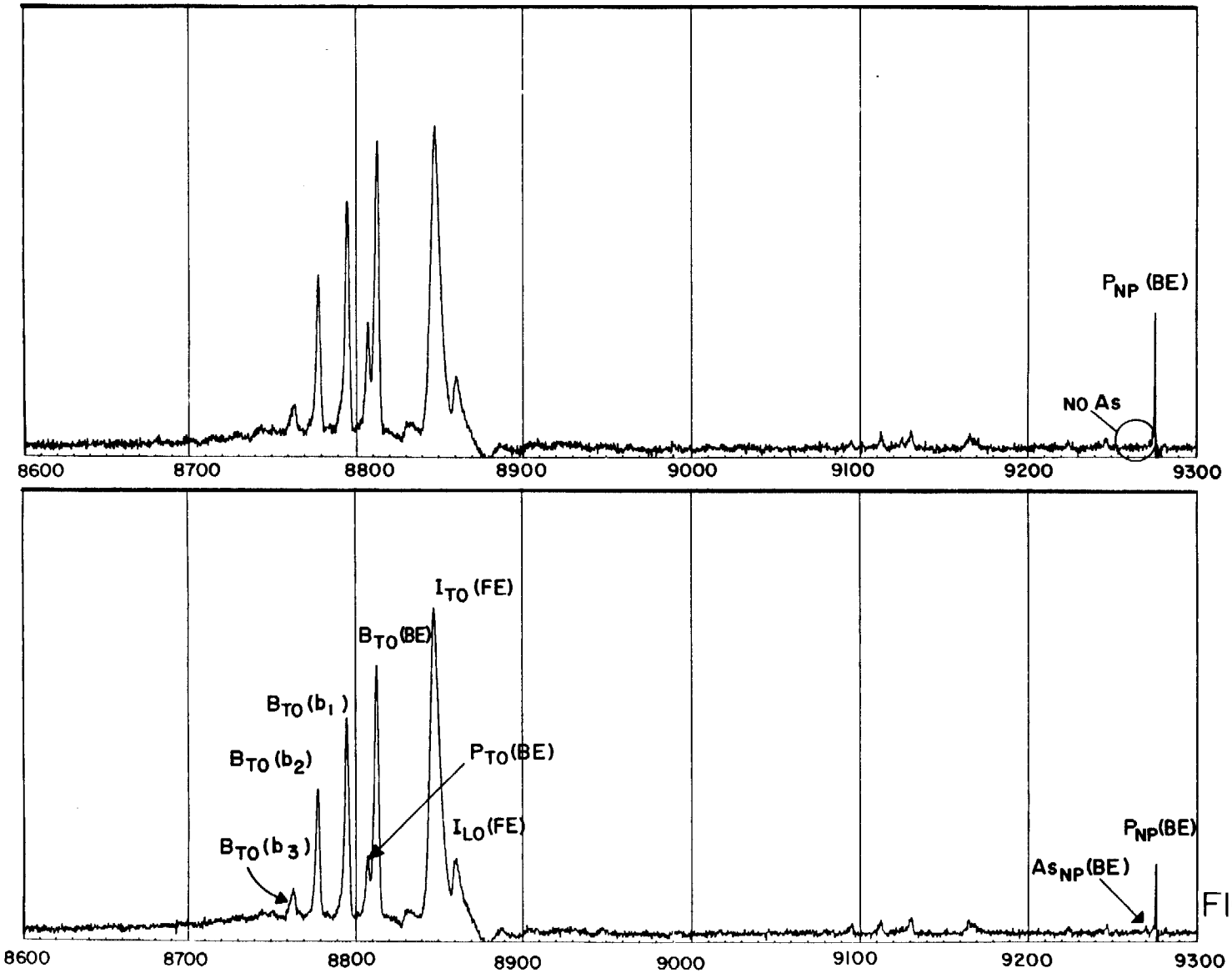

FIGS. 15A-15C illustrate the performance of the FTPL system in a particularly complex and subtle aspect of PL analysis. This aspect is the "competitive" nature of the different impurities in silicon in PL analysis. FIGS. 15A-15C show FTPL-produced spectrographs based on three different silicon samples, each having essentially the same concentration of boron. (This information is derived both from the boron quantity predicted from the sample manufacturing process, and from bulk analysis of the silicon samples using standard transmission-type spectroscopy). In all three figures, the laser power on the sample was 16 mW; and the resolution was 0.56 $cm^{-1}$.

In FIGS. 15A and 15B, the boron concentration signals identified as $B_{TO}$(BE) are of substantially the same height as the intrinsic signals identified as $I_{TO}$(FE). However, in FIG. 15C, the boron signal is significantly lower than the intrinsic signal. It appears that this boron signal difference in FIG. 15C is caused by the presence of arsenic in this sample, as indicated by the signal identified as $AS_{NP}$(BE) in the no-phonon region.

Figure 16:
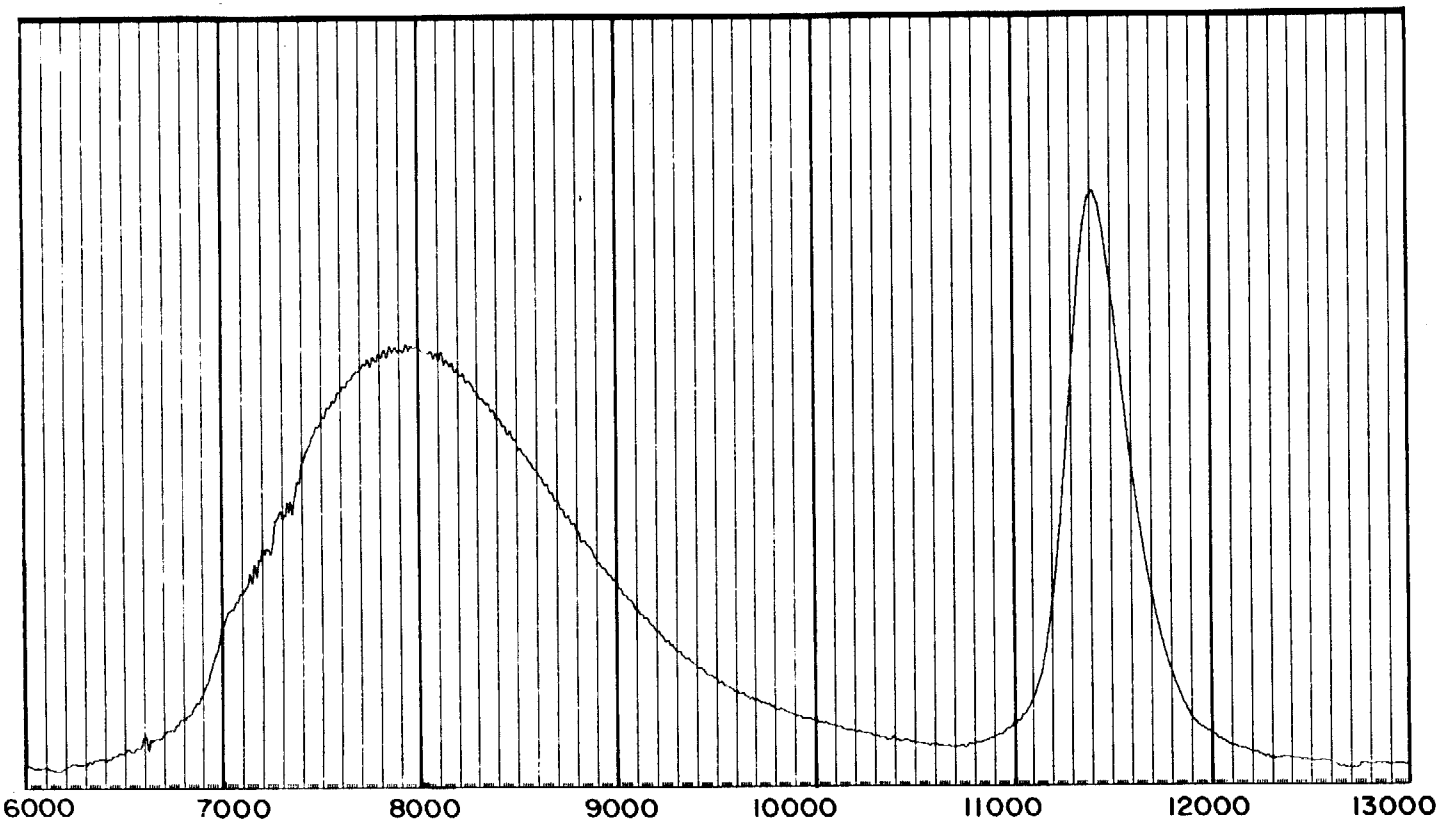
FIG. 16 is a wide-band spectrograph illustrating the characteristics of a sample of gallium arsenide, as recorded by the FTPL system.

FIG. 16 is included as an example of a spectrograph produced by the FTPL system having extremely wide spectral coverage, extending from 6000 wave numbers to 13000 wave numbers. The material analyzed in FIG. 16 is gallium arsenide doped with tellurium. The germanium diode detector tends to drop off at the lower end of the spectrum in FIG. 16, particularly below 6500 wave numbers.

From the foregoing description, it will be apparent that the apparatus and method disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

In some of the claims, quantified minimum values are stated of one or more of the four primary characteristics—sensitivity, resolution, spectral coverage, and speed of data acquisition. The purpose of such claims is to enhance the differentiation from prior art photoluminescence analysis systems. The figures used have necessarily been chosen arbitrarily, because the present invention represents differences in degree of performance of such magnitude that they become, in effect, differences in kind; but there are no dramatic change-over points. For example, referring to resolution capability, a broader resolution claim value "no coarser than two wave numbers", and a narrower claim value "approximately one-half wave number", have been specified. Referring to the width of a spectral scan, a broader claim value of "at least from 8600 to 9300 wave numbers", and a narrower claim value of "from 6500 to 13,500 wave numbers", have been specified. Referring to speed of data acquisitions, a broader value of "requiring accumulated data during a period no longer than six minutes", and a narrower value "only requires accumulated data obtained during a period of three minutes", have been specified. And referring to sensitivity, a broader value of "a signal-to-noise sensitivity ratio of at least 25", and a narrowr value of "a signal-to-noise sensitivity ratio of at least 100", have been specified.

What is claimed is:

1. An apparatus, for photo-luminescent analysis of [impurities in] a sample, comprising:

means for applying *laser* radiation to the surface of the sample to cause emission of photons by the sample;

*the sample having significant photon emissivity within the radiation wavelength range of 0.8 to 1.4 microns;* means for collecting the sample-emitted photons and providing a photon beam for interferometer input;

an interferometer which receives the input photon beam and outputs a spectrally encoded photon beam; and a detector which receives the interferometer output beam and converts it into electronic signals.

2. The apparatus of claim 1 wherein the sample is crystalline silicon.

3. The apparatus of claim [2] *1* wherein: the interferometer output beam includes radiation wavelengths within the range of 0.8 to 1.4 microns; and the detector's quantum efficiency in response to radiation wavelengths in the range of 0.8 to 1.4 microns is substantially flat.

4. The apparatus of claim 3 wherein the detector is a germanium photo-detector.

5. The apparatus of claim 4 which also comprises:

a cooling container enclosing the germanium photodetector and maintaining it at a temperature no greater than approximately that of liquid nitrogen; and a pre-amplifier also enclosed in the container and having as its input the electronic signal output of the detector.

6. The apparatus of claim 3 which also comprises:

means for preventing radiation other than sample-emitted photons from reaching the detector.

7. The apparatus of claim 1 which also comprises:

means for preventing radiation other than sample-emitted photons from reaching the detector.

8. An apparatus, for photo-luminescent analysis of [impurities at] the surface of a sample, comprising:

means for supplying *laser* excitation radiation to the surface of the sample, for the purpose of causing the sample to emit photons;

*the sample having significant photon emissivity within the radiation wavelength range of 0.8 to 1.4 microns;*

*cooling means for the sample containing liquid helium in which the sample is immersed;* means for collecting sample-emitted photons and providing an output photon radiation beam;

an interferometer beamsplitter to which said photon radiation beam is directed, and which partially reflects and partially transmits the photon radiation beam;

two reflecting means, one fixed and one movable for scanning purposes, which reflect back to the beamsplitter its partially reflected and partially transmitted photon beams; and a detector which receives a recombined photon beam from the beamsplitter, and which converts the intensity of that beam into electronic output signals.

9. The apparatus of claim 8 which also comprises:

a monochromatic radiation subsystem, including a source of such radiation, which subsystem is caused by operation of the interferometer to provide clocking signals which determine the frequency of sampling of detector output signals; and means for preventing the monochromatic radiation from affecting the photon radiation beam, including means for substantially enclosing the source of the monochromatic radiation and filtering means which limits the radiation from the source to the wavelength required for the clocking function.

10. The apparatus of claim 9 which also comprises:

a broad band radiation subsystem, including a source of such radiation, which subsystem is caused by operation of the interferometer to provide a scan starting signal for the analysis of the photon radiation beam entering the interferometer; and means for preventing the wide band radiation from affecting the photon radiation beam, including means for turning off the wide band source during each scan of the photon radiation beam, and means for turning on the wide beam source between successive scans of the photo radiation beam.

11. The apparatus of claim 10 which also comprises:

means associated with the detector for substantially preventing it from receiving radiation outside a certain desired range; and means for covering the entire photo-luminescent, interferometer, and detector, apparatus, in order to isolate it from ambient atmospheric and radiation conditions.

12. The apparatus of claim 9 which also comprises:

means associated with the detector for substantially preventing it from receiving radiation outside a certain desired range; and means for covering the entire photo-luminescent, interferometer, and detector apparatus, in order to isolate it from ambient atmospheric and radiation conditions.

13. The apparatus of claim 8 which also comprises:

a broad band radiation subsystem, including a source of such radiation, which subsystem is caused by operation of the interferometer to provide a scan starting signal for the analysis of the photon radiation beam entering the interferometer; and means for preventing the wide band radiation from affecting the photon radiation beam, including means for turning off the wide band source during each scan of the photon radiation beam, and means for turning on the wide band source between successive scans of the photon radiation beam.

14. The apparatus of claim 8 which also comprises:

means associated with the detector for substantially preventing it from receiving radiation outside a certain desired range; and means for covering the entire photo-luminescent, interferometer, and detector, apparatus, in order to isolate it from ambient atmospheric and radiation conditions.

15. The apparatus of claim 8 which also comprises:

a cooling container enclosing the detector and maintaining it at a temperature substantially that of liquified nitrogen; and electronic circuitry located in the cooling container which receives the electronic output signal from the detector and provides a first stage of preamplification of those signals.

16. The apparatus of claim 15 in which the detector is a germanium photo-diode having a substantially flat range of sensitivity to radiation from 0.8 micron wavelength to 1.4 micron wavelength.

17. The apparatus of claim 8 in which the detector is a germanium photo-diode having a substantially flat range of sensitivity to radiation from 0.8 micron wavelength to 1.4 micron wavelength.

18. [The apparatus of claim 8 wherein] *An apparatus, for photo-luminescent analysis of impurities at the surface of a sample, comprising:*

*means for supplying excitation radiation to the surface of the sample, for the purpose of causing the sample to emit photons;*

*means for collecting sample-emitted photons and providing an output photon radiation beam;*

*an interferometer beamsplitter to which said photon radiation beam is directed, and which partially reflects and partially transmits the photon radiation beam;*

*two reflecting means, one fixed and one movable for scanning purposes, which reflect back to the beamsplitter its partially reflected and partially transmitted photon beams; and*

*a detector which receives a recombined photon beam from the beamsplitter, and which converts the intensity of that beam into electronic output signals;* the sample [is] *being* crystalline silicon and the radiation wavelengths to be analyzed [are] *being* in the neighborhood of 1.1 microns.

19. The apparatus of claim 8 wherein:

the means for supplying concentrated radiation to the surface of the sample is an argon ion laser beam perpendicular to the surface of the sample; and the means for collecting the sample-emitted photons is a lens (or lens system) having an aperture through which the argon ion laser beam passes on its way to the sample.

20. The apparatus of claim 19 which also comprises:

a mirror which directs the photon radiation beam from the sample toward the beamsplitter, and which has an aperture through which (a) the argon ion laser beam passes on its way to the sample and (b) specular reflection from the sample exits the system.

21. [The apparatus of claim 8 which also comprises:] *An apparatus, for photo-luminescent analysis of impurities at the surface of a sample, comprising:*

*means for supplying excitation radiation to the surface of the sample, for the purpose of causing the sample to emit photons;*

*means for collecting sample-emitted photons and providing an output photon radiation beam;*

*an interferometer beamsplitter to which said photon radiation beam is directed, and which partially reflects and partially transmits the photon radiation beam;*

*two reflecting means, one fixed and one movable for scanning purposes, which reflect back to the beamsplitter its partially reflected and partially transmitted photon beams;*

*a detector which receives a recombined photon beam from the beamsplitter, and which converts the intensity of that beam into electronic output signals; and* means for deriving from the detector's electronic output signals a spectrograph having a resolution no coarser than two wave numbers.

22. The apparatus of claim 21 wherein the resolution is approximately one-half wave number.

23. The apparatus of claim 21 wherein the spectrograph has a scan width extending at least from 8600 to 9300 wave numbers.

24. The apparatus of claim 23 wherein:

the spectrograph requires accumulated data from successive scans obtained during a period no longer than six minutes; and the spectrograph has a signal-to-noise sensitivity ratio of at least 25.

25. The apparatus of claim 21 wherein the spectrograph requires accumulated data from successive scans obtained during a period no longer than six minutes.

26. The apparatus of claim 21 wherein the spectrograph has a signal-to-noise sensitivity ratio of at least 25.

27. [The apparatus of claim 8 which also comprises:] *An apparatus, for photo-luminescent analysis of impurities at the surface of a sample, comprising:*

*means for supplying excitation radiation to the surface of the sample, for the purpose of causing the sample to emit photons;*

*means for collecting sample-emitted photons and providing an output photon radiation beam;*

*an interferometer beamsplitter to which said photon radiation beam is directed, and which partially reflects and partially transmits the photon radiation beam:*

*two reflecting means, one fixed and one movable for scanning purposes, which reflect back to the beamsplitter its partially reflected and partially transmitted photon beams;*

*a detector which receives a recombined photon beam from the beamsplitter, and which converts the intensity of that beam into electronic output signals; and* means for deriving from the detector's electronic output signals a spectrograph having a scan width extending at least from 8600 to 9300 wave numbers.

28. The apparatus of claim 27 wherein the spectrograph has a scan width extending from 6500 to 13,500 wave numbers.

29. The apparatus of claim 27 wherein the spectrograph requires accumulated data from successive scans obtained during a period no longer than six minutes.

30. The apparatus of claim 27 wherein the spectrograph has a signal-to-noise sensitivity ratio of at least 25.

31. [The apparatus of claim 8 which also comprises:] *An apparatus, for photo-luminescent analysis of impurities at the surface of a sample, comprising:*

*means for supplying excitation radiation to the surface of the sample, for the purpose of causing the sample to emit photons;*

*means for collecting sample-emitted photons and providing an output photon radiation beam;*

*an interferometer beamsplitter to which said photon radiation beam is directed, and which partially reflects and partially transmits the photon radiation beam;*

*two reflecting means, one fixed and one movable for scanning purposes, which reflect back to the beamsplitter its partially reflected and partially transmitted photon beams;*

*a detector which receives a recombined photon beam from the beamsplitter, and which converts the intensity of that beam into electronic output signals; and* means for deriving from the detector's electronic output signals a spectrograph requiring accumulated data from successive scans obtained during a period no longer than six minutes.

32. The apparatus of claim 31 wherein the spectrograph only requires accumulated data obtained during a period of three minutes.

33. The apparatus of claim 31 wherein the spectrograph has a signal-to-noise sensitivity ratio of at least 25.

34. [The apparatus of claim 8 which also comprises:] *An apparatus, for photo-luminescent analysis of impurities at the surface of a sample, comprising:*

*means for supplying excitation radiation to the surface of the sample, for the purpose of causing the sample to emit photons;*

*means for collecting sample-emitted photons and providing an output photon radiation beam;*

*an interferometer beamsplitter to which said photon radiation beam is directed, and which partially reflects and partially transmits the photon radiation beam;*

*two reflecting means, one fixed and one movable for scanning purposes, which reflect back to the beamsplitter its partially reflected and partially transmitted photon beams;*

*a detector which receives a recombined photon beam from the beamsplitter, and which converts the intensity of that beam into electronic output signals; and* means for deriving from the detector's electronic output signals a spectrograph having a signal-to-noise sensitivity ratio of at least 25.

35. The apparatus of claim 32 wherein the spectrograph has a signal-to-noise sensitivity ratio of at least 100.

36. A method of calibrating spectrographic analysis of samples based on photoluminescence data which comprises:

directing a laser beam having a certain power at the surface of a sample;

collecting the photons from the sample caused by the laser excitation;

passing the collected photons through a Fourier Transform spectrometer to provide a spectrograph;

determining from the spectrograph whether there is substantial electron-hole-droplet formation in the sample at the selected laser beam power; and repeating the foregoing steps until that laser beam power has been essentially determined at which electronhole-droplet formation in the sample is substantially stabilized.

37. The method of claim 36 in which the laser power used for successive spectrographs is gradually reduced until the effect of formation of electron-hole-droplets has been substantially stabilized on the spectrograph.

38. The method of claim 37 in which subsequent spectrographs taken of the sample use substantially the maximum laser power which produces stabilized electron-hole-droplet formation.

39. A method of obtaining new information from spectrographic analysis of samples based on photoluminescence data which comprises:

directing a laser beam having a certain power at the surface of a sample;

collecting the photons from the sample caused by the laser excitation;

passing the collected photons through a Fourier Transform spectrometer to provide a spectrograph;

the spectral coverage extending into sufficiently high frequencies to include the no-phonon region;

the resolution of the spectrographic data being sufficiently fine to identify one or more impurity materials in the no-phonon region that are not identifiable in the lower frequency portions of the spectrum.

40. The method of claim 39 in which the fineness of resolution is approximately one-half wave number.

41. The method of using photoluminescence to analyze [impurities at] the surface of a sample, comprising the following steps:

supplying *laser* excitation radiation to the surface of the sample, thereby causing the sample to emit photons *within the radiation wavelength range of 0.8 to 1.4 microns:* collecting the sample-emitted photons;

using such photons to provide an output photon radiation beam;

directing that beam to an interferometer beamsplitter, which partially reflects and partially transmits the photon radiation beam, [thereby creating] *so as to create* two photon beams; reflecting one of such photon beams back to the beamsplitter from a fixed reflecting means;

reflecting the other of such photon beams back to the beamsplitter from a moving reflecting means;

recombining the photon beams at the beamsplitter to provide a spectrally scanned output beam; and directing the scanned photon output beam to a detector which converts it into electronic output signals.

42. The method of claim 41 which also comprises: blocking substantially all radiation from the detector except the photon beam from the beamsplitter.

43. The method of claim 41 which also comprises: deriving from the detector's electronic output signals a spectrograph having a resolution no coarser than two wave numbers.

44. The method of claim 41 which also comprises: deriving from the detector's electronic output signals a spectrograph having a scan width extending at least from 8600 to 9300 wave numbers.

45. The method of claim 41 which also comprises: deriving from the detector's electronic output signals a spectrograph requiring accumulated data from successive scans obtained during a period no longer than six minutes.

46. The method of claim 41 which also comprises: deriving from the detector's electronic output signals a spectrograph having a signal-to-noise sensitivity ratio of at least 25.

* * * * *